(12) United States Patent
Chen et al.

(10) Patent No.: US 10,815,196 B2
(45) Date of Patent: Oct. 27, 2020

(54) (S)-CSA SALT OF S-KETAMINE, (R)-CSA SALT OF S-KETAMINE AND PROCESSES FOR THE PREPARATION OF S-KETAMINE

(71) Applicant: Janssen Pharmaceutica NV, Beerse (BE)

(72) Inventors: Cheng Yi Chen, Schaffhausen (CH); Oliver Floegel, Zürich (CH); Michael Justus, Schaffhausen (CH); Adrian Maurer, Schaffhausen (CH); Karl Reuter, Gundelfingen (DE); Tobias Strittmatter, Schaffhausen (CH); Tobias Wedel, Karlsruhe (DE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/997,267

(22) Filed: Jun. 4, 2018

(65) Prior Publication Data
US 2018/0282266 A1    Oct. 4, 2018

Related U.S. Application Data

(63) Continuation of application No. 15/152,705, filed on May 12, 2016, now abandoned.

(60) Provisional application No. 62/160,659, filed on May 13, 2015.

(51) Int. Cl.
C07C 309/23    (2006.01)
C07C 309/19    (2006.01)
C07C 225/20    (2006.01)

(52) U.S. Cl.
CPC .......... *C07C 309/23* (2013.01); *C07C 225/20* (2013.01); *C07C 309/19* (2013.01); *C07B 2200/07* (2013.01); *C07B 2200/13* (2013.01); *C07C 2601/14* (2017.05); *C07C 2602/42* (2017.05); *H05K 999/99* (2013.01)

(58) Field of Classification Search
None
See application file for complete search history.

(56) References Cited

U.S. PATENT DOCUMENTS

| | | | |
|---|---|---|---|
| 5,543,434 A | 8/1996 | Weg | |
| 6,008,357 A | 12/1999 | Tickner et al. | |
| 6,040,331 A * | 3/2000 | Yamamoto | C07D 209/90 514/228.2 |
| 6,040,479 A | 3/2000 | Steiner et al. | |
| 6,176,242 B1 | 1/2001 | Rise | |
| 7,273,889 B2 | 9/2007 | Mermelstein et al. | |
| 7,687,080 B2 | 3/2010 | Wolicki | |
| 7,973,043 B2 | 7/2011 | Migaly | |
| 2003/0212143 A1* | 11/2003 | Torres/Russo | C07C 221/00 514/649 |
| 2004/0214215 A1 | 10/2004 | Yu et al. | |
| 2006/0276550 A1 | 12/2006 | Bhagwat | |
| 2007/0287753 A1 | 12/2007 | Charney et al. | |
| 2009/0275759 A1* | 11/2009 | Maragni | C07D 495/04 549/23 |
| 2009/0306137 A1 | 12/2009 | Wolfgang et al. | |
| 2011/0112131 A1 | 5/2011 | Holtman et al. | |
| 2011/0306674 A1 | 12/2011 | Schiene et al. | |
| 2012/0225949 A1 | 9/2012 | Papalos | |
| 2013/0123320 A1* | 5/2013 | Chervinsky | A61K 45/06 514/401 |
| 2013/0172361 A1 | 7/2013 | Fava et al. | |
| 2013/0236573 A1 | 9/2013 | Singh et al. | |
| 2014/0093592 A1 | 4/2014 | Singh et al. | |
| 2014/0256821 A1 | 9/2014 | Charney et al. | |
| 2016/0332962 A1 | 11/2016 | Chen et al. | |
| 2016/0338977 A1 | 11/2016 | Singh et al. | |

FOREIGN PATENT DOCUMENTS

| | | |
|---|---|---|
| CL | 1996 | 7/1996 |
| DE | 2062620 | 7/1971 |
| DE | 4312016 A1 | 10/1994 |
| DE | 19619665 A1 | 11/1997 |
| DE | 102007009888 A1 | 9/2008 |
| EP | 1103256 A1 | 5/2001 |
| JP | 51-095036 A | 8/1976 |
| JP | 63-002932 A | 1/1988 |
| JP | 63-014771 A | 1/1988 |
| JP | 63-192753 A | 8/1988 |
| JP | 2015-078181 A | 4/2015 |
| WO | 94/23711 A1 | 10/1994 |
| WO | 96/11894 A1 | 4/1996 |
| WO | 00/04875 A2 | 2/2000 |
| WO | 2007/111880 A2 | 10/2007 |
| WO | 2011/020061 A2 | 2/2011 |
| WO | 2014/031975 A1 | 2/2014 |
| WO | 2014/143646 A1 | 9/2014 |
| WO | 2014/152196 A1 | 9/2014 |
| WO | 2014/169272 A1 | 10/2014 |

OTHER PUBLICATIONS

Wikipedia, Esketamine, Wikipedia, Sep. 1, 2015, pp. 1-4, Wikipedia.
White, et al., Comparative Pharmacology of ketamine Isomers, British Journal of Anaesthesia, 1985, pp. 197-203, vol. 57 Issue 2.
White et al, Pharmacology of Ketamine Isomers in surgical Patients, Anesthesiology, 1980, pp. 231-239, vol. 52, The American Society of Anesthesiologists.
Washington, et al., Determination of baseline human nasal pH and the effect of intranasally administered buffers, International Journal of Pharmaceutics, Nov. 24, 1999, pp. 139-146, vol. 198, Elsevier Science B.V.

(Continued)

*Primary Examiner* — Sudhakar Katakam
*Assistant Examiner* — Jennifer C Sawyer
(74) *Attorney, Agent, or Firm* — BakerHostetler

(57) ABSTRACT

The present invention is directed to processes for the preparation of esketamine. The present invention is further directed to processes for the resolution of S-ketamine from a racemic or enantiomerically enriched mixture of ketamine. The present invention is further directed to an (S)-CSA salt of S-ketamine, more particularly a monohydrate form of the (S)-CSA salt of S-ketamine; and to an (R)-CSA salt of R-ketamine.

15 Claims, 1 Drawing Sheet

(56) References Cited

OTHER PUBLICATIONS

Vranken et al, Iontophoretic administration of S(C)-ketamine in patients with intractable central pain: A placebo-controlled trial, Pain, Aug. 15, 2005, pp. 224-231, vol. 118, Elsevier B.V.
Tansey et al., Contribution of Common Genetic Variants to Antidepressant Response, Biol. Psychiatry, 2013, pp. 679-682, 73.
Stevenson, Ketamine:A Review, Update in Anaesthesia, 2005, pp. 25-29, vol. 20.
Soni,et al., Safety assessment of propyl paraben: a review of the published literature, Food and Chemical Toxicology, Sep. 25, 2000, pp. 513-532, vol. 39, Elsevier Science LTD.
Soni,et al., Safety assessment of esters of p-hydroxybenzoic acid parabens, Food and Chemical Toxicology, Jan. 31, 2005, pp. 985-1015, vol. 43, Elsevier Ltd.
Skolnick et al, Glutamate-based antidepressants: 20 years on, Trends in Pharmacological Sciences, 2006, pp. 563-569, vol. 30 Issue 11.
Sarchiapone, et al., Association of Polymorphism (Val66met) of Brain-Derived Neurotrophic Factor with Suicide Attempts in Depressed Patients, Neuropsychobiology, Jul. 7, 2008, pp. 139-145, vol. 57.
Salvadore G Ed—Sanacora Gerard et al: "Impact of the Va166Met Polymorphism of Brain-Derived Neurotrophic Factor on Esketamine and Ketamine Antidepressant Effects in Patients with Treatment-Resistant Depression", Biological Psychiatry, Elsevier Science, New York, NY; US, vol. 77, No. 9 supplement, May 1, 2015 (May 1, 2015), p. 360S.
Price et al, Effects of Intravenous Ketamine on Explicit and Implicit Measures of Suicidality in Treatment-Resistant Depression, Biol. Psychiatry, 2009, pp. 522-526, vol. 66, Society of Biological Psychiatry.
PRD3253CLPCT_Opposition Brief Translation, 2014.
Pfizer, (S)-(+)-Ketamine Hydrochloride Solution, Material Safety Data Sheet, Nov. 5, 2008, pp. 1-8, Version 1.0.
Paul et al, Comparison of racemic ketamine and S-ketamine in treatment-resistant major depression: Report of two cases, The World Journal of Biological Psychiatry,, Sep. 28, 2007, pp. 241-244, vol. 10 Issue 3, Informa UK Ltd.
Paslakis et al, Oral Administration of the NMDA Receptor Antagonist S-Ketamine as Add-On Therapy of Depression: A Case Series, Pharmacopsychiatry, 2010, pp. 33-35, vol. 43.
Okamoto et al, Rapid Antidepressant Effect of Ketamine Anesthesia During Electroconvulsive Therapy of Treatment-Resistant Depression, Journal of ECT, 2010, pp. 223-227, vol. 26 Issue 3, Lippincott Williams & Wilkins.
Oishi, et al., Effects of propyl paraben on the male reproductive system, Food and Chemical Toxicology, Jul. 7, 2002, pp. 1807-1813, vol. 40, Elsevier Science Ltd.
Noppers et al, Absence of long-term analgesic effect from a short-term S-ketamine infusion on fibromyalgia pain: A randomized, prospective, double blind, active placebo-controlled trial, European Journal of Pain, Apr. 11, 2011, pp. 942-949, vol. 15, Elsevier Ltd.
Mathew et al, Ketamine for Treatment-Resistant Unipolar Depression, CNS Drugs, 2012, pp. 189-204, vol. 26 Issue 3, Adis Data Information BV.
Marhofer, et al, S(+)-Ketamine for caudal block in paediatric anaesthesia, British Journal of Anaesthesia, 2000, pp. 341-345, vol. 84 Issue 3.
Logan, et al., Immobilizing Wild Mountain Lions (Felis Concolor) with Ketamine hydrochloride and Xylazine Hydrochloride, Journal of Wildlife Diseases, 1986, pp. 97-103, vol. 22 Issue 1.
Johansson, et al., Prehospital analgesia using nasal administration of S-ketamine-a case series, Scandinavian Journal of Trauma, 2013, pp. 1-5, vol. 21 Issue 38, BioMed Central Ltd.
International Search Report re: PCT/US2016/33404 dated Aug. 16, 2016.
International Search Report re: PCT/US2015/44830 dated Nov. 23, 2015.
International Search Report re: PCT/US2015/049961 dated Jan. 12, 2016.
International Search Report re: PCT/US2014/027074 dated May 27, 2014.
International Search Report re: PCT/US2014/027059 dated Jul. 16, 2014.
International Search Report re: PCT/US2013/030476 dated Apr. 24, 2013.
International Search Report re: PCT/EP2016/060922 dated Jul. 28, 2016.
Huge, et al., Effects of low-dose intranasal (S)-ketamine in patients with neuropathic pain, European Journal of Pain, Sep. 3, 2009, pp. 387-394, vol. 14, Elsevier Ltd.
Huang, et al., Mechanism of Nasal Absorption of Drugs I: Physicochemical Parameters Influencing the Rate of In Situ Nasal Absorption of Drugs in Rats, Journal of Pharmaceutical Science, Feb. 27, 1985, pp. 608-611, vol. 74 Issue 6.
Hong, et al., Allergy to ophthalmic preservatives, Current Opinion in Allergy and Clinical Immunology, 2009, pp. 447-453, vol. 9.
Ho, et al., In vitro effects of preservatives in nasal sprays on human nasal epithelial cells, American Journal of Rhinology, 2008, pp. 125-129, vol. 22.
Hijazi, et al., Stability of Ketamine and Its Metabolites Norketamine and Dehydronorketamine in Human Biological Samples, Clinical Chemistry, 2001, pp. 1713-1715, vol. 47 Issue 9.
Gonzalo Laje et al: "Correspondence Brain-Derived Neurotrophic Factor Val66Met Polymorphism and Antidepressant Efficacy of Ketamine in Depressed Patients", Biol Psychiatry, vol. 72, No. 11, Dec. 1, 2012 (Dec. 1, 2012), pp. e27-e28.
Gomes, et al., Neurotoxicity of Subarachnoid Preservative-Free S(+)-Ketamine in Dogs, Pain Physician, 2011, pp. 83-90, vol. 14.
GENBANK_AC099753, *Homo sapiens* chromosome 3 clone RP11-466A13, complete sequence. Mar. 20, 2002, [online]. [Retrieved on Oct. 1, 2015]. Retrieved from the Internet: <URL: http://www.ncbi.nlm.nih.gov/nuccore/19551144/> PDF file: p. 1-40. p. 1, Definition; p. 3, Origin, p. 27, the nucleotide sequence between 113924-112924, especially the nucleotides between 113444-113405; and the nucleotide at the position of 113424.
Diazgranados et al, Rapid Resolution of Suicidal ideation After a Single Infusion of an N-Methyl-D Aspartate Antagonist in Patient With Treatment-Resistant Major Depressive Disorder, J Clin Psychiatry, 2010, pp. 1605-1611, vol. 71 Issue 12, Physicians Postgraduate Press.
Clinical trials.gov _NCT01998958, A Study to Evaluate the Safety and Efficacy of Intranasal Esketamine in Treatment-resistant Depression. ClinicalTrials.gov Identifier: NCT01998958. Jul. 14, 2014 [online]. [Retrieved on Sep. 23, 2015]. Retrieved from the Internet: <URL: https://clinicaltrials.gov/archive/NCT01998958/2014_07 14> PDF File: p. 1-40. p. 1, Brief Summary, Phase, and the last para; and p. 2, para 1 and 3.
Anonymous: "NCT02133001 on Jun. 23, 2014: ClinicalTrials.gov Archive", Jun. 23, 2014 (Jun. 23, 2014), pp. 1-6, XP055230128, Retrieved from the Internet: URL:https://clinicaltrials.gov/archive/NCT 02133001/2014_06_23.
Aboul-Enein, et al.; Enantiomeric Separation of Ketamine Hydrochloride in Pharmaceutical Formulation and Human Serum by Chiral Liquid Chromatography, Journal of Liquid Chromatography, 15(18), 3285-3293, 1992.
Bhushan, et al.; (2008). Direct TLC Resolution of (±)-Ketamine and (±)-Lisinopril by Use of (+)-Tartaric Acid or (−)-Mandelic Acid as Impregnating Reagents or Mobile Phase Additives. Isolation of the Enantiomers, Chromatographia, 68(11-12), 1045-1051.
Hong, et al.; (1982). Stereochemical Studies of Demethylated Ketamine Enantiomers, Journal of Pharmaceutical Sciences, 71(8), 912-914, 1982.
Li, et al.; Resolution of Ketamine Enantiomers by HPLC with Two-phases Discrimination, Chinese Journal of Pharmaceutical Analysis; 2005 (11), 1339-1342.
Nguyen, et al.; Chiral Drugs: An Overview, Int J Biomed Sci. Jun. 2006; 2(2): 85-100.
Theurillat, et al.; Enantioselective analysis of ketamine and its metabolites in equine plasma and urine by CE with multiple isomer sulfated ß-CD. Electrophoresis, 2007, 28(15), 2748-2757.

* cited by examiner

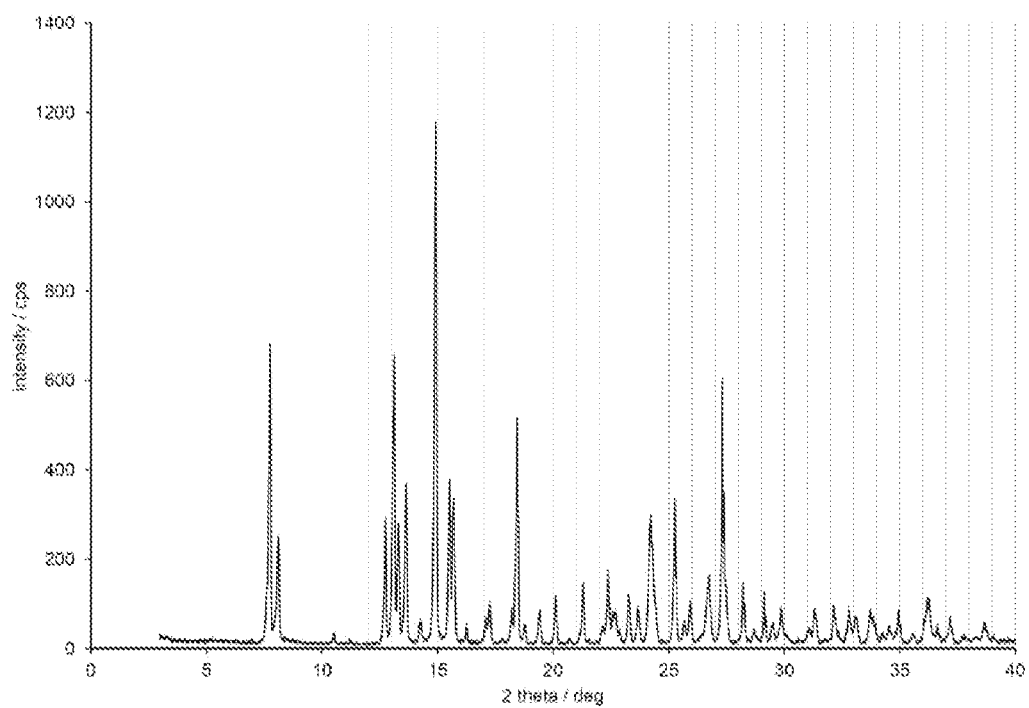
pXRD for Crystalline, Monohydrate (S)-CSA salt of S-Ketamine

(S)-CSA SALT OF S-KETAMINE, (R)-CSA SALT OF S-KETAMINE AND PROCESSES FOR THE PREPARATION OF S-KETAMINE

CROSS REFERENCE TO RELATED APPLICATIONS

This application is a continuation application of U.S. patent application Ser. No. 15/152,705 filed May 12, 2016, and claims the benefit of U.S. Provisional Application No. 62/160,659 filed May 13, 2015, the entire disclosures of each of which are hereby incorporated in their entirety.

FIELD OF THE INVENTION

The present invention is directed to processes for the preparation of (S)-ketamine. The present invention is further directed to processes for the resolution of S-ketamine from a racemic or enantiomerically enriched mixture of ketamine. The present invention is further directed to an (S)-CSA salt of S-ketamine, more particularly a monohydrate form of the (S)-CSA salt of S-ketamine; and to an (R)-CSA salt of R-ketamine.

BACKGROUND OF THE INVENTION

Ketamine (a racemic mixture of the corresponding S- and R-enantiomers) is an NMDA receptor antagonist, with a wide range of effects in humans, including analgesia, anesthesia, hallucinations, dissociative effects, elevated blood pressure and bronchodilation. Ketamine is primarily used for the induction and maintenance of general anesthesia. Other uses include sedation in intensive care, analgesia (particularly in emergency medicine and treatment of bronchospasms. Ketamine has also been shown to be efficacious in the treatment of depression (particularly in those who have not responded to current anti-depressant treatment). In patients with major depressive disorders, ketamine has additionally been shown to produce a rapid antidepressant effect, acting within hours.

The S-ketamine enantiomer (or S-(+)-ketamine or esketamine) has higher potency or affinity for the NMDA receptor and thus potentially allowing for lower effective dosages; and is available for medical use, administered either IV (intravenously) or IM (intramuscularly), under the brand name KETANEST S.

HUDYMA, T. W., et al., in DE 2062620 A published Jul. 15, 1971 describe resolution of ketamine with natural L-tartaric acid. Hudyma et al further disclose that attempts at resolution of ketamine with cam phorsulfonic acid (CSA) were unsuccessful. STEINER K., et al., in DE 19619665 C2 published Mar. 8, 2001 (US Equiv. U.S. Pat. No. 6,040,479) describe a process for resolution of ketamine using L-tartaric acid in water or a mixture of water and an alcohol and/or ketone, ether or ester. RUSSO, T., et al., in PCT Publication WO2001/098265 (US Equiv. Patent Publication No. 20030212143 A1), published Aug. 15, 2002 describe chiral resolution of ketamine using L-tartaric acid in a mixture of solvent and water.

There remains a need for a method for the resolution of the S-ketamine enantiomer from racemic ketamine, wherein (a) the process does not use chiral tartaric acid; (b) the process comprises one to three, preferably one to two crystallization steps (for example, to avoid loss of yield); (c) the process results in a yield of greater than about 25%; (d) the process uses solvents which are non-toxic and/or do not require special handling; and/or (e) the process is suitable for large scale or commercial manufacture.

SUMMARY OF THE INVENTION

The present invention is directed to a process for the preparation of a monohydrate form of (S)-camphorsulfonic acid salt of S-ketamine (preferably a crystalline monohydrate form), a compound of formula (I-CSA)

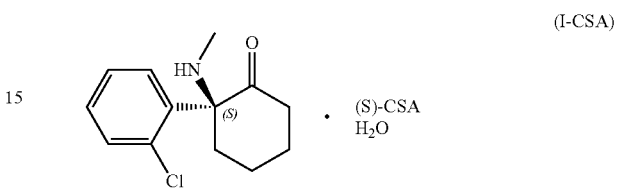

(also known by its IUPAC name of (S)-2-(2-chlorophenyl)-2-(methylammonium)cyclohexanone(+)-camphorsulfonate monohydrate), comprising

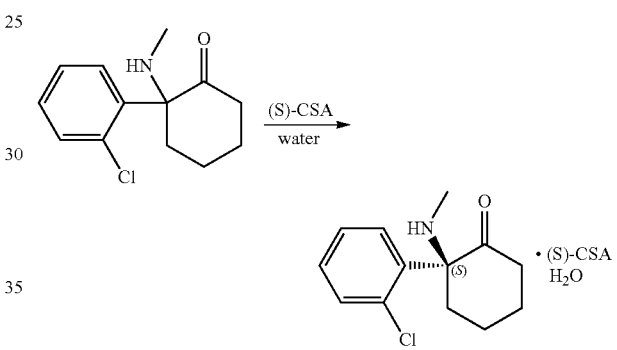

reacting ketamine (preferably racemic ketamine) with (S)-camphorsulfonic acid, a known compound, wherein the (S)-camphorsulfonic acid is present in an amount in the range of from about 0.5 to about 2.0 molar equivalents (relative to the moles of ketamine);
in the presence of water; wherein the water is present in an amount in the range of from about 3.5% to about 15%;
in an organic solvent; at a temperature in the range of from about 20° C. to about solvent reflux temperature;
to yield the monohydrate form of (S)-CSA salt of S-ketamine;
wherein the monohydrate form of (S)-CSA salt of S-ketamine is present in an enantiomeric excess in the range of from about 50% to about 100%.

The present invention is further directed to a process for the preparation of S-ketamine hydrochloride (also known as esketamine), a compound of formula (I-HCl)

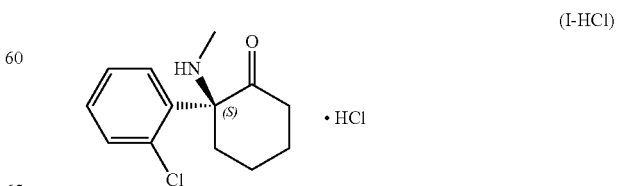

comprising the steps of (a) reacting the monohydrate form of (S)-camphorsulfonic acid salt of S-ketamine (prepared for example as described above) with an inorganic base; in a solvent or mixture of solvents; preferably in the presence of water; to yield S-ketamine as a free base; and (b) reacting the S-ketamine free base with HCl; to yield the corresponding S-ketamine hydrochloride salt.

The present invention is directed to a process for the preparation of (R)-camphorsulfonic acid salt of R-ketamine (preferably a crystalline form), a compound of formula (II-CSA)

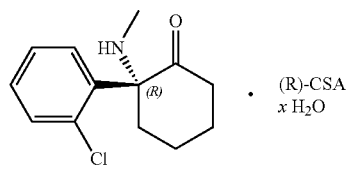

comprising

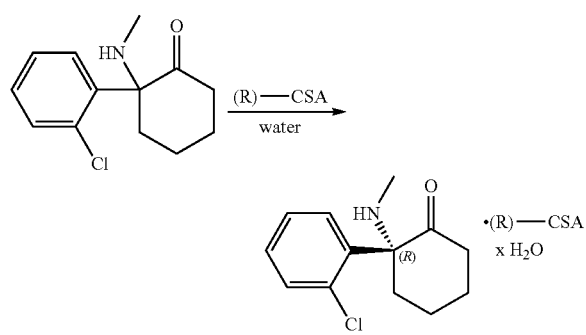

reacting ketamine (preferably racemic ketamine) with (R)-camphorsulfonic acid, a known compound, wherein the (R)-camphorsulfonic acid is present in an amount in the range of from about 0.5 to about 2.0 molar equivalents (relative to the moles of ketamine);

in the presence of water; wherein the water is present in an amount in the range of from about 3.5% to about 15%;

in an organic solvent; at a temperature in the range of from about 20° C. to about solvent reflux temperature;

to yield a product mixture comprising an (R)-CSA salt of R-ketamine, preferably as a solid, more preferably as a hydrate (for example as a monohydrate), and S-ketamine; wherein the S-ketamine remains in solution;

wherein the (R)-CSA salt of R-ketamine is present in an enantiomeric excess in the range of from about 50% to about 100%.

The present invention is further directed to a process for the preparation of S-ketamine hydrochloride (also known as esketamine), a compound of formula (I-HCl)

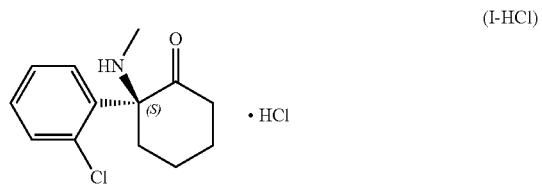

comprising the steps of

Step 1:

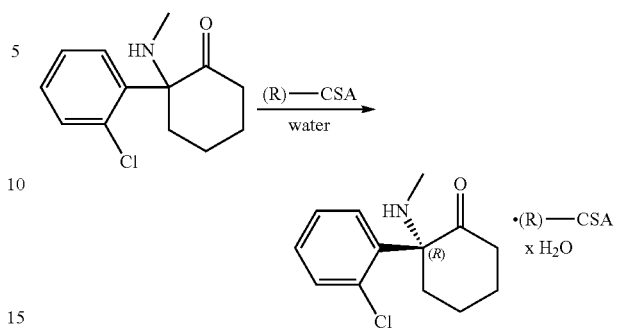

reacting ketamine (preferably racemic ketamine) with (R)-camphorsulfonic acid, a known compound, wherein the (R)-camphorsulfonic acid is present in an amount in the range of from about 0.5 to about 2.0 molar equivalents (relative to the moles of ketamine);

in the presence of water; wherein the water is present in an amount in the range of from about 3.5% to about 15%;

in an organic solvent; at a temperature in the range of from about 20° C. to about solvent reflux temperature;

to yield a product mixture comprising an (R)-CSA salt of R-ketamine, preferably as a hydrate (for example, as a monohydrate), preferably as a solid, and S-ketamine; wherein the S-ketamine remains in solution; and wherein the (R)-CSA salt of R-ketamine is present in an enantiomeric excess in the range of from about 50% to about 100%

Step 2:

filtering the product mixture (of Step 1) to yield the (R)-camphorsulfonic acid salt of R-ketamine as a solid and a filtrate comprising S-ketamine;

Step 3: reacting the S-ketamine (in the filtrate or optionally, isolated from the filtrate, by, for example, reacting with a suitably selected inorganic base and extracting with a suitably selected organic solvent) with HCl; to yield the corresponding S-ketamine ketamine hydrochloride salt.

The present invention is further directed to a monohydrate form of (S)-CSA salt of S-ketamine, preferably a crystalline monohydrate form of (S)-CSA salt of S-ketamine, as described in detail hereinafter.

The present invention is further directed to an (R)-CSA salt of R-ketamine, preferably a crystalline form of (R)-CSA salt of R-ketamine, as described in detail hereinafter.

The present invention is further directed to a product prepared according to any of the processes described herein.

Illustrative of the invention is a pharmaceutical composition comprising a pharmaceutically acceptable carrier and a product prepared according to any of the process(es) described herein. An illustration of the invention is a pharmaceutical composition made by mixing a product prepared according to any of the process(es) described herein and a pharmaceutically acceptable carrier.

Illustrating the invention is a process for making a pharmaceutical composition comprising mixing a product prepared according to any of the process(es) described herein and a pharmaceutically acceptable carrier.

Exemplifying the invention are methods of treating a disorder mediated treatment resistant depression comprising administering to a subject in need thereof a therapeutically effective amount of a product prepared according to any of the process(es) described herein.

In an embodiment, the present invention is directed to a product prepared according to any of the process(es) described herein for use as a medicament. In another embodiment, the present invention is directed to a product prepared according to any of the process(es) described herein for use in the treatment of treatment resistant depression. In another embodiment, the present invention is directed to a composition comprising a product prepared according to any of the process(es) described herein for the treatment of treatment resistant depression.

Another example of the invention is the use of a product prepared according to any of the process(es) described herein in the preparation of a medicament for treating treatment resistant depression, in a subject in need thereof. In another example, the present invention is directed to a product prepared according to any of the process(es) described herein for use in a methods for treating treatment resistant depression, in a subject in need thereof.

BRIEF DESCRIPTIONS OF THE FIGURES

FIG. 1 illustrates a pXRD spectra for a representative sample of the crystalline, monohydrate form of the (S)-CSA salt of S-ketamine.

DETAILED DESCRIPTION OF THE INVENTION

The present invention is directed to process(es) for the preparation of S-ketamine, S-ketamine hydrochloride, S-ketamine•(S)-CSA salt (the (S)-CSA salt of S-ketamine) and a monohydrate (preferably crystalline) form of S-ketamine•(S)-CSA salt. The present invention is directed to process(es) for the preparation of R-ketamine•(R)-CSA salt (the (R)-CSA salt of R-ketamine), preferably a crystalline form of R-ketamine•(R)-CSA salt. The present invention is further directed to process(es) for the resolution of S-ketamine from a racemic (or enantiomerically enriched mixture) of ketamine.

The present invention is further directed to an (S)-CSA salt of S-ketamine, preferably, a monohydrate (S)-CSA salt of S-ketamine, more preferably, a crystalline monohydrate (S)-CSA salt of S-ketamine. The present invention is further directed to an (R)-CSA salt of R-ketamine, preferably, a crystalline (R)-CSA salt of R-ketamine. The present invention is further directed to any CSA salt as described herein.

As used herein, unless otherwise noted, the term "ketamine" shall mean a racemic or enantiomerically enriched mixture of ketamine, a compound of the following structure

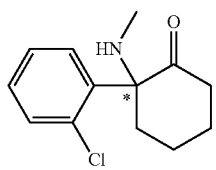 [SMILES: CNC1(c2ccccc2Cl)CCCCC1=O]

also known as 2-(2-chlorophenyl)-2-(methylamino)cyclohexanone. As used herein, unless otherwise noted, the term "enantiomerically enriched mixture" shall mean a mixture of the corresponding (S)- and (R)- enantiomers, wherein one of said enantiomers is present in an enantiomeric excess of greater than about 50%, preferably present in an enantiomeric excess in the range of from about 50% to about 95%, or any amount or range therein, preferably, in an enantiomeric excess in the range of from about 75% to about 95%.

In an embodiment of the present invention, the ketamine is racemic. In another embodiment of the present invention, the ketamine is an enantiomerically enriched mixture, wherein the (S)- or (R)- enantiomer is present in an enantiomeric excess of greater than about 50%, preferably, in an enantiomeric excess in the range of from about 50% to about 99%, or any amount or range therein, for example, in an enantiomeric excess of about 51%, 55%, 60%, 60%, 65%, 70%, 75%, 80%, 85%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5% or 99%.

As used herein, unless otherwise noted, the term "S-ketamine" shall mean the (S)-enantiomer of ketamine, as a free base, a compound of formula (I)

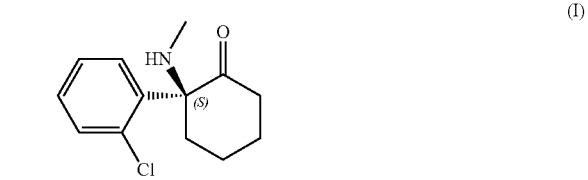

also known as (S)-2-(2-chlorophenyl)-2-(methylamino)cyclohexanone. In an embodiment, S-ketamine is present in an enantiomeric excess of greater than about 50%, or any amount or range therein, more preferably in an enantiomeric excess of greater than about 75%, more preferably in an enantiomeric excess of greater than about 85%, more preferably in an enantiomeric excess in the range of from about 90% to about 100%, or any amount or range therein, more preferably in an enantiomeric excess in the range of from about 95% to about 99%, for example, in an enantiomeric excess of about 90%, 90.5%, 91%, 91.5%, 92%, 92.5%, 93%, 93.5%, 94%, 94.5%, 95%, 95.5%, 96%, 96.5%, 97%, 97.5%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9% or 100%.

As used herein, unless otherwise noted, the term "esketamine" shall mean the hydrochloric acid salt of (S)-enantiomer of ketamine, a compound of formula (I-HCl)

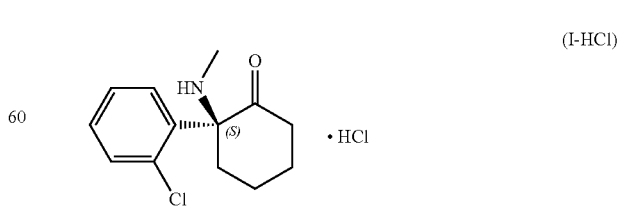

also known as (S)-2-(2-chlorophenyl)-2-(methylamino) cyclohexanone hydrochloride.

As used herein, unless otherwise noted, the term "R-ketamine" shall mean the (R)-enantiomer of ketamine, as a free base, a compound of formula (II)

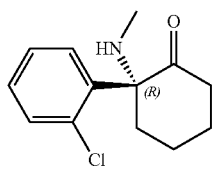

also known as (R)-2-(2-chlorophenyl)-2-(methylamino) cyclohexanone. In an embodiment, R-ketamine is present in an enantiomeric excess of greater than about 50%, or any amount or range therein, more preferably in an enantiomeric excess of greater than about 75%, more preferably in an enantiomeric excess of greater than about 85%, more preferably in an enantiomeric excess in the range of from about 90% to about 100%, or any amount or range therein, more preferably in an enantiomeric excess in the range of from about 95% to about 99%, for example, in an enantiomeric excess of about 90%, 90.5%, 91%, 91.5%, 92%, 92.5%, 93%, 93.5%, 94%, 94.5%, 95%, 95.5%, 96%, 96.5%, 97%, 97.5%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9% or 100%.

As used herein, unless otherwise noted the term "S-CSA" shall mean (+)-camphorsulfonic acid, also known as (1S, 4R)-camphorsulfonic acid. As used herein, unless otherwise noted, the term "R-CSA" shall mean (−)-camphorsulfonic acid, also known as (1R,4S)-camphorsulfonic acid. (Camphorsulfonic acid is also known by its IUPAC name (7,7-dimethyl-2-oxobicyclo[2.2.1]heptan-1-yl)methanesulfonic acid.)

In an embodiment, the present invention is directed to methods for the treatment of treatment-refractory or treatment-resistant depression, wherein a product prepared according to any of the process(es) described herein is administered at a dosage amount in the range of from about 0.01 mg to about 1000 mg, or any amount or range therein, preferably from about 0.01 mg to about 500 mg, or any amount or range therein, preferably from about 0.1 mg to about 250 mg, or any amount or range therein. In another embodiment, the present invention is directed to methods for the treatment of treatment-refractory or treatment-resistant depression, wherein a product prepared according to any of the process(es) described herein is administered at a dosage amount in the range of from about 0.01 mg to about 1000 mg, preferably selected from the group consisting of 0.01 mg, 0.025 mg, 0.05 mg, 0.1 mg, 0.5 mg, 1 mg, 5 mg, 10 mg, 25 mg, 50 mg, 100 mg, 150 mg, 200 mg, 250 mg and 500 mg.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, it is intended that within the scope of the present invention, any element, in particular when mentioned in relation to a compound of formula (I), shall comprise all isotopes and isotopic mixtures of said element, either naturally occurring or synthetically produced, either with natural abundance or in an isotopically enriched form. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. Radiolabelled compounds of formula (I) may comprise a radioactive isotope selected from the group of $^3H$, $^{11}C$, $^{18}F$, $^{122}I$, $^{123}I$ $^{125}I$, $^{131}I$, $^{75}Br$, $^{76}Br$, $^{77}Br$ and $^{82}Br$. Preferably, the radioactive isotope is selected from the group of $^3H$, $^{11}C$ and $^{18}F$.

Abbreviations used in the specification, particularly the Schemes and Examples, are as follows:
CPME=Cyclopentyl methyl ether
CSA=Camphorsulfonic acid (IUPAC name (7,7-dimethyl-2-oxobicyclo[2.2.1]heptan-1-yl)methanesulfonic acid)
DCM=Dichloromethane
DMF=N,N-Dimethylformamide
DMSO=Dimethyl sulfoxide
DSC=Dynamic Scanning Calorimetry
DVS=Dynamic Vapor Sorption
ee or % e.e.=Enantiomeric Excess
$^1H$ NMR=Hydrogen Nuclear Magnetic Resonance
MeOH=Methanol
MEK=Methyl ethyl ketone
2-Me-THF=2-Methyl-tetrahydrofuran
ML-Mother Liquor
2-PrOH or IPA=2-Propanol (Isopropanol)
pXRD=Powder X-Ray Doffraction
% RH=% Relative Humidity
RT=Room temperature
TBME or MTBE=tert-Butyl methyl ether
TG-FTIR=ThermoGravimetric-Fourier Transform Infra-Red (Spectroscopy)
THF=Tetrahydrofuran
v:v=volume:volume ratio As used herein, unless otherwise noted, the term "isolated form" shall mean that the compound is present in a form which is separate from any solid mixture with another compound(s), solvent system or biological environment. In an embodiment of the present invention, a product prepared according to any of the process(es) described herein is present in an isolated form. In another embodiment, the (S)-CSA salt of S-ketamine, preferably the monohydrate form of the (S)-CSA salt of S-ketamine, more preferably the crystalline monohydrate form of the (S)-CSA salt of S-ketamine, is present in an isolated form. In another embodiment, the (R)-CSA salt of R-ketamine, preferably the crystalline form of the (R)-CSA salt of R-ketamine, is present in an isolated form.

As used herein, unless otherwise noted, the term "substantially pure form" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment of the present invention, a product prepared according to any of the process(es) described herein is present as a substantially pure form. In another embodiment, the (S)-CSA salt of S-ketamine, preferably the monohydrate form of the (S)-CSA salt of S-ketamine, more preferably the crystalline monohydrate form of the (S)-CSA salt of S-ketamine, is present as a substantially pure form. In another embodiment, the (R)-CSA salt of R-ketamine, preferably a crystalline form of the (R)-CSA salt of R-ketamine, is present as a substantially pure form.

As used herein, unless otherwise noted, the term "substantially free of a corresponding salt form(s)" when used to described the compound of formula (I) shall mean that mole percent of the corresponding salt form(s) in the isolated base of formula (I) is less than about 5 mole percent, preferably less than about 2 mole percent, more preferably, less than about 0.5 mole percent, most preferably less than about 0.1 mole percent. In an embodiment of the present invention, a product prepared according to any of the process(es) described herein is present in a form which is substantially free of corresponding salt form(s). In another embodiment, the (S)-CSA salt of S-ketamine, preferably the monohydrate form of the (S)-CSA salt of S-ketamine, more preferably the crystalline monohydrate form of (S)-CSA salt of S-ketamine, is present in a form which is substantially free of corresponding salt form(s). In another embodiment, the (R)-CSA salt of R-ketamine, preferably a crystalline form of the (R)-CSA salt of R-ketamine, is present in a form which is substantially free of corresponding salt form(s).

As used herein, the term "treatment-refractory or treatment-resistant depression" and the abbreviation "TRD" shall be defined as major depressive disorder that does not respond to adequate courses of at least two antidepressants, preferably two or more antidepressants, more preferably two to three, antidepressants.

One skilled in the art will recognize that the failure to respond to an adequate course of a given antidepressant may be determined retrospectively or prospectively. In an embodiment, at least one of the failures to respond to an adequate course of antidepressant is determined prospectively. In another embodiment, at least two of the failures to respond to an adequate course of antidepressant are determined prospectively. In another embodiment, at least one of the failures to respond to an adequate course of antidepressant is determined retrospectively. In another embodiment, at least two of the failures to respond to an adequate course of antidepressant are determined retrospectively.

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (co-morbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

Optimal dosages to be administered may be readily determined by those skilled in the art, and will vary with the particular compound or compounds used, the mode of administration, the strength of the preparation and the advancement of the disease condition. In addition, factors associated with the particular patient being treated, including patient's sex, age, weight, diet, time of administration and concomitant diseases, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

As used herein, the term "composition" is intended to encompass a product comprising the specified ingredients in the specified amounts, as well as any product which results, directly or indirectly, from combinations of the specified ingredients in the specified amounts.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

Wherein the enantiomeric excess expressions recited herein state that the % ee is greater than about X %, said expression is understood to mean a range from an enantiomeric excess of greater than about X % to about 100%, or any amount or range therein.

Examples of suitable solvents, bases, reaction temperatures, and other reaction parameters and components are provided in the detailed description which follows herein. One skilled in the art will recognize that the listing of said examples is not intended, and should not be construed, as limiting in any way the invention set forth in the claims which follow thereafter.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems. One skilled in the art will further recognize that wherein two consecutive reaction or process steps are run without isolation of the intermediate product (i.e. the product of the first of the two consecutive reaction or process steps), then the first and second reaction or process steps may be run in the same solvent or solvent system; or alternatively may be run in different solvents or solvent systems following solvent exchange, which may be completed according to known methods.

One skilled in the art will further recognize that the reaction or process step(s) as herein described (or claimed) are allowed to proceed for a sufficient period of time until the reaction is complete, as determined by any method known to one skilled in the art, for example, chromatography (e.g. HPLC). In this context a "completed reaction or process step" shall mean that the reaction mixture contains a significantly diminished amount of the starting material(s)/reagent(s) and a significantly reduced amount of the desired product(s), as compared to the amounts of each present at the beginning of the reaction.

Chiral HPLC against a standard may be used to determine percent enantiomeric excess (% ee). The enantiomeric excess may be calculated as follows $$[(Rmoles-Smoles)/(Rmoles+Smoles)]\times 100\%$$

where Rmoles and Smoles are the R and S mole fractions in the mixture such that Rmoles+Smoles=1. The enantiomeric excess may alternatively be calculated from the specific rotations of the desired enantiomer and the prepared mixture as follows:

$$ee=([\alpha-obs]/[\alpha-max])\times 100.$$

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, cam phorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (x)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Resolution of Ketamine (General Methods)

The present invention is directed to a process for the resolution of ketamine into its enantiomers, and more particularly, to processes for the preparation of an (S)-CSA salt of S-ketamine and an HCl salt of S-ketamine, as described in more detail in Scheme 1, below.

Scheme 1

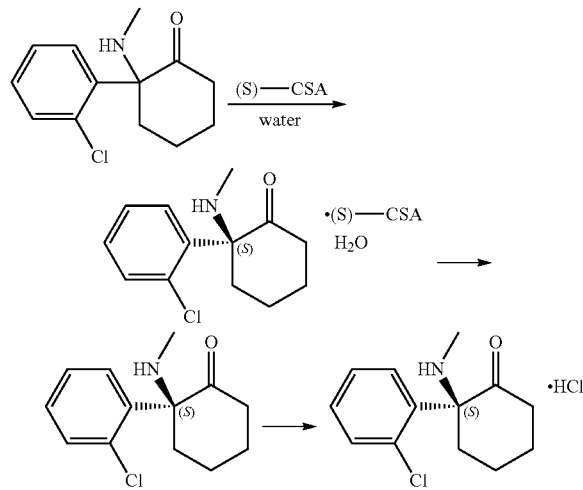

Accordingly, ketamine (preferably racemic ketamine) is reacted with (S)-camphorsulfonic acid (also known as (+)-CSA or S-CSA)), a known compound; wherein the (S)-CSA is present in an amount in the range of from about 0.5 to about 2.0 molar equivalents (relative to the amount of ketamine), or any amount or range therein, preferably in an amount in the range of from about 0.75 to about 1.2 molar equivalents, more preferably, in an amount in the range of from about 0.9 to about 1.1 molar equivalents, more preferably, in an amount of about 1 molar equivalent;

in the presence of water; wherein the water is present in an amount in the range of from about 3.5% to about 15% (by weight in the solvent), or any amount or range therein, preferably in an amount in the range of from about 3.8% to about 11%, more preferably in an amount in the range of from about 5% to about 10%, more preferably in an amount in the range of from about 6% and about 8% (for example about 6.7%);

in a suitably selected organic solvent such as a suitably selected ether (for example a cyclic ether) such as THF, 2-methyl-THF, and the like, or a suitably selected ketone such as methyl ethyl ketone, acetone, methyl isobutyl ketone, and the like, preferably methyl ethyl ketone or 2-methyl-THF, more preferably 2-methyl-THF; at a temperature in the range of from about 20° C. to about solvent reflux temperature, or any temperature or range therein, preferably at a temperature in the range of from about 30° C. to about 100° C., more preferably at a temperature in the range of from about 50° C. to about 80° C. (for example at about 70° C., at about 75° C., at about 80° C., at about 100° C.);

to yield the corresponding monohydrate (S)-CSA salt of S-ketamine, preferably as a solid, more preferably as a crystalline solid; wherein the monohydrate (S)-CSA salt of S-ketamine is preferably present in an enantiomeric excess of greater than about 50%, preferably in an enantiomeric excess in the range of from about 50% to about 100%, or any amount or range therein, more preferably, in an enantiomeric excess in the range of from about 75% to about 100%, more preferably, more preferably, in an enantiomeric excess in the range of from about 80% to about 100%, more preferably, in an enantiomeric excess in the range of from about 90% to about 100%, more preferably, in an enantiomeric excess in the range of from about 98% to about 100%. In an example, the monohydrate (S)-CSA salt of S-ketamine is prepared in an enantiomeric excess of greater than or equal to about 90%. In another example, the monohydrate (S)-CSA salt of S-ketamine is prepared in an enantiomeric excess of greater than or equal to about 96%.

Preferably, the monohydrate (S)-CSA salt of S-ketamine is isolated by known methods, for example by filtration.

One skilled in the art will recognize that the product mixture resulting from the above reaction of ketamine with (S)-CSA will comprise the monohydrate (S)-CSA salt of S-ketamine (as a precipitate or suspension) and R-ketamine (protonated, in solution). Further, one skilled in the art will recognize, that following filtration of the monohydrate (S)-CSA salt of S-ketamine, the mother liquor or filtrate will comprise enantiomerically enriched R-ketamine.

The monohydrate (S)-CSA salt of S-ketamine is optionally recrystallized, according to known methods, from a suitably selected solvent or mixture of solvents, (for example from THF, methyl ethyl ketone or a mixture of THF and water), preferably in the presence of (or in a mixture with) water.

The monohydrate (S)-CSA salt of S-ketamine is further optionally reacted with a suitably selected base, preferably an inorganic base such as $K_2CO_3$, $Na_2CO_3$, $NaHCO_3$, NaOH, KOH, and the like, preferably $K_2CO_3$; wherein the base is preferably present in an amount in the range of from about 1.0 to about 10 molar equivalents (relative to the moles of the monohydrate (S)-CSA salt of S-ketamine), preferably in the range of from about 1.0 to about 5.0 molar equivalents, more preferably in a range of from about 1.0 to about 2.0 molar equivalents (for example, about 1.2 molar equivalents);

in a suitably selected solvent such as isopropyl acetate, ethyl acetate, toluene, and the like, preferably isopropyl acetate; preferably a solvent which is not miscible with water; to yield the corresponding S-ketamine, as a free base. One skilled in the art will recognize that the enantiomeric excess of the S-ketamine base will be approximately equal to the enantiomeric excess of the monohydrate (S)-CSA salt of S-ketamine, since the reaction with the inorganic base would not be expected to affect the stereo-center (e.g. result in racemization at the stereo-center).

Preferably, the S-ketamine free base is isolated according to known methods, for example by filtration.

The S-ketamine free base is further optionally reacted, according to known methods, with a suitably selected acid such as HCl (for example as HCl gas), to yield the corresponding acid addition salt, preferably the corresponding hydrochloride salt. One skilled in the art will recognize that the enantiomeric excess of the S-ketamine salt, preferably the S-ketamine hydrochloride salt will be approximately equal to or greater than the enantiomeric excess of the S-ketamine, since the reaction with the suitably selected acid would not be expected to affect the stereo-center (e.g. result in racemization at the stereo-center).

In an embodiment of the present invention, the S-ketamine free base is reacted with the acid, preferably HCl, wherein the amount of the acid is in the range of from about 0.8 to about 5.0 molar equivalents (relative to the moles of S-ketamine base), more preferably in an amount in the range of rom about 1.0 to about 3.0 molar equivalents, more preferably in an amount in the range of from about 1.0 to about 1.5 molar equivalents (for example about 1.2 molar equivalents).

The present invention is further directed to a process for the resolution of ketamine into its enantiomers, and more particularly, to a process for the preparation of an (R)-CSA salt of R-ketamine and an HCl salt of S-ketamine, as described in more detail in Scheme 2, below.

Scheme 2

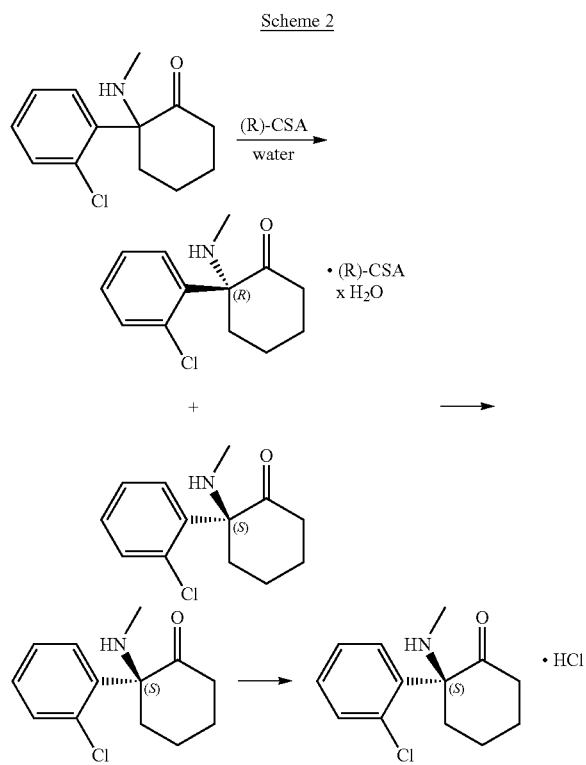

Accordingly, ketamine (preferably racemic ketamine) is reacted with (R)-camphorsulfonic acid (also known as (–)-CSA or R-CSA)), a known compound; wherein the (R)-CSA is present in an amount in the range of from about 0.5 to about 2.0 molar equivalents (relative to the amount of ketamine), or any amount or range therein, preferably in an amount in the range of from about 0.75 to about 1.5 molar equivalents, for example in an amount of about 1.0 molar equivalents;

in the presence of water; wherein the water is present in an amount in the range of from about 3.5% to about 15% (by weight in the solvent), or any amount or range therein, preferably in an amount in the range of from about 7.5% to about 12.5%, for example in an amount of about 9%;

in a suitably selected organic solvent such as a suitably selected ether (for example a cyclic ether) such as THF, 2-methyl-THF, and the like, or a suitably selected ketone such as methyl ethyl ketone, acetone, methyl isobutyl ketone, and the like, preferably methyl ethyl ketone or 2-methyl-THF, more preferably 2-methyl-THF; at a temperature in the range of from about 20° C. to about solvent reflux temperature, or any temperature or range therein, preferably at a temperature in the range of from about 30° C. to about 100° C.;

to yield a product mixture comprising (a) the corresponding (R)-CSA salt of R-ketamine, preferably, as a hydrate (for example, as a monohydrate), preferably as a solid, more preferably as a crystalline solid (for example, as a precipitate); wherein the (R)-CSA salt of R-ketamine is preferably present in an enantiomeric excess of greater than about 50%, preferably in an enantiomeric excess in the range of from about 50% to about 100%, or any amount or range therein, more preferably, in an enantiomeric excess in the range of from about 75% to about 100%, more preferably, in an enantiomeric excess of about 96%, more preferably, in an enantiomeric excess in the range of from about 98% to about 100%; and (b) S-ketamine; wherein the S-ketamine remains in solution; wherein the S-ketamine is preferably present in an enantiomeric excess of greater than about 50%, preferably in an enantiomeric excess in the range of from about 50% to about 100%, or any amount or range therein, more preferably, in an enantiomeric excess in the range of from about 75% to about 100%, more preferably, in an enantiomeric excess of about 96%, more preferably, in an enantiomeric excess in the range of from about 98% to about 100%.

Although not intended to be limiting or definitive, it is theorized that the S-ketamine, which remains in solution in the product mixture described above, may present in a protonated base form (protonated by any excess (R)-CSA present).

Preferably, the (R)-CSA salt of R-ketamine is isolated according to known methods, for example by filtration. One skilled in the art will recognize that filtration of the product mixture will yield the (R)-CSA salt of R-ketamine as a solid and a filtrate or mother liquor comprising S-ketamine.

The S-ketamine is then further optionally isolated from the filtrate or mother liquor (according to known methods, for example by reacting with a suitably selected inorganic base such as $K_2CO_3$, $Na_2CO_3$, $NaHCO_3$, NaOH, KOH, and the like, and further extracting with a suitably selected organic solvent, preferably an organic solvent which is not miscible with water, such as 2-methyl-THF, isopropyl acetate, and the like, preferably isopropyl acetate) and/or reacted (according to known methods), with a suitably selected acid such as HCl (for example as HCl gas), to yield the corresponding acid addition salt, preferably the corresponding hydrochloride salt. One skilled in the art will recognize that the enantiomeric excess of the S-ketamine salt, preferably the S-ketamine hydrochloride salt will be approximately equal to or greater than the enantiomeric excess of the S-ketamine, since the reaction with the suitably selected acid would not be expected to affect the stereo-center (e.g. result in racemization at the stereo-center).

In an embodiment of the present invention, the S-ketamine is reacted with the acid, preferably HCl, wherein the amount of the acid is in the range of from about 0.8 to about 5.0 molar equivalents (relative to the moles of S-ketamine base), more preferably in an amount in the range of rom about 1.0 to about 3.0 molar equivalents, more preferably in an amount in the range of from about 1.0 to about 1.5 molar equivalents (for example about 1.2 molar equivalents).

Crystalline Forms

The crystalline forms of the present invention, for example the monohydrate form of the (S)-CSA salt of S-ketamine may be characterized by, for example, powder X-Ray Diffraction (pXRD), TG-FTIR, DSC, DVS, Karl-Fischer analysis, optical rotation, and other known methods for determining the physical properties of a solid or crystal.

The powder X-ray diffractograms (diffraction spectra, pXRD) provided herein were measured using on an X-ray diffractometer using CuKα radiation. The pestled sample was back-loaded into a conventional x-ray holder. The sample was scanned from 3 to 40°2θ with a step size of 0.01°2θ and a time per step of 5.0 seconds. Instrument voltage and current settings were 40 kV and 30 mA.

ThermoGravimetric-Fourier Transform InfraRed (TG-FTIR) measurements, where carried out were measures using a Netzsche Thermo-Microbalance TG209 with Bruker FT-IR Spectrometer Vector 22, with aluminum crucible with microhoel, nitrogen atmosphere and scanning form 25° C. to 300° C. at a heating rate of 10K/min.

Dynamic Scanning calorimetry (DSC) measurements (where completed) were measured using either (a) Perkins Elmer DSC 7, hermetically closed gold crucible, measuring from 20° C. to 270° C. at a heating rate of 10K/min, (b) TA Instruments DSC Q2000, hermetically closed gold crucible, measuring from 20° C. to 300° C. at a heating rate of 10K/min.

Dynamic Vapor Sorption (DVS) measurements (where completed) were measured using a Projekt Messtechnik Sorptions Prufsystem SPS 11 or Surface Measurement Systems DVS-1 scanning (cycling relative humidity and hodling the sample at a set relative humidity) as follow: (a) holding sample at 50% RH for 2 hours; (b) 50% RH to 0% RH (5%/h); holding at 0% RH for 5 hours; (c) 0% RH to 95% RH (5%/h); holding at 95% RH for 5 hours; and (d) 95% RH to 50% RH (5%/h); holding at 50% RH for 2 hours.

A powder XRD (pXRD) diffractogram was measured for multiple samples of the crystalline monohydrate form of (S)-CSA salt of S-ketamine (prepared as described herein), with a representative example as shown in FIG. 1. The crystalline monohydrate form of (S)-CSA salt of S-ketamine, may be characterized by its X-ray diffraction pattern, comprising peaks having a relative intensity greater than or equal to about 5%, as listed in Table 1, below.

TABLE 1 pXRD Peaks for Monohydrate (S)-CSA salt of S-Ketamine

| position [°2θ] | d-spacing [Å] | relative intensity [%] |
|---|---|---|
| 7.76 | 11.38 | 58.03 |
| 8.11 | 10.89 | 21.58 |
| 12.75 | 6.94 | 24.89 |
| 13.13 | 6.74 | 55.99 |
| 13.31 | 6.65 | 23.96 |
| 13.64 | 6.49 | 31.52 |
| 14.92 | 5.93 | 100.00 |
| 15.51 | 5.71 | 32.12 |
| 15.71 | 5.64 | 28.46 |
| 17.09 | 5.18 | 6.03 |
| 17.26 | 5.13 | 8.92 |
| 18.20 | 4.87 | 7.73 |
| 18.45 | 4.80 | 43.84 |
| 19.43 | 4.56 | 7.39 |
| 20.10 | 4.41 | 10.03 |
| 21.29 | 4.17 | 12.49 |
| 22.38 | 3.97 | 14.87 |
| 22.58 | 3.93 | 6.88 |
| 22.71 | 3.91 | 7.31 |
| 23.26 | 3.82 | 10.45 |
| 23.66 | 3.76 | 7.90 |
| 24.22 | 3.67 | 25.66 |
| 25.26 | 3.52 | 28.46 |
| 25.68 | 3.47 | 5.35 |
| 25.93 | 3.43 | 8.92 |
| 26.76 | 3.33 | 13.93 |

TABLE 1-continued pXRD Peaks for Monohydrate (S)-CSA salt of S-Ketamine

| position [°2θ] | d-spacing [Å] | relative intensity [%] |
|---|---|---|
| 27.33 | 3.26 | 51.32 |
| 28.21 | 3.16 | 12.32 |
| 29.13 | 3.06 | 11.05 |
| 29.85 | 2.99 | 7.90 |
| 31.31 | 2.86 | 7.48 |
| 32.12 | 2.78 | 8.24 |
| 32.79 | 2.73 | 7.90 |
| 33.10 | 2.70 | 6.20 |
| 33.72 | 2.66 | 7.48 |
| 34.95 | 2.56 | 7.48 |
| 36.20 | 2.48 | 9.77 |
| 37.17 | 2.42 | 6.03 |

In an embodiment, the crystalline monohydrate form of (S)-CSA salt of S-ketamine is characterized by its pXRD pattern which comprises peaks having a relative intensity greater than or equal to about 10%, as listed in Table 2, below.

TABLE 2 pXRD Peaks for Monohydrate (S)-CSA salt of S-Ketamine

| position [°2θ] | d-spacing [Å] | relative intensity [%] |
|---|---|---|
| 7.76 | 11.38 | 58.03 |
| 8.11 | 10.89 | 21.58 |
| 12.75 | 6.94 | 24.89 |
| 13.13 | 6.74 | 55.99 |
| 13.31 | 6.65 | 23.96 |
| 13.64 | 6.49 | 31.52 |
| 14.92 | 5.93 | 100.00 |
| 15.51 | 5.71 | 32.12 |
| 15.71 | 5.64 | 28.46 |
| 18.45 | 4.80 | 43.84 |
| 21.29 | 4.17 | 12.49 |
| 22.38 | 3.97 | 14.87 |
| 23.26 | 3.82 | 10.45 |
| 24.22 | 3.67 | 25.66 |
| 25.26 | 3.52 | 28.46 |
| 26.76 | 3.33 | 13.93 |
| 27.33 | 3.26 | 51.32 |
| 28.21 | 3.16 | 12.32 |
| 29.13 | 3.06 | 11.05 |

In another embodiment, the crystalline monohydrate form of (S)-CSA salt of S-ketamine is characterized by its pXRD pattern which comprises peaks having a relative intensity greater than or equal to about 20%, as listed in Table 3, below.

TABLE 3 pXRD Peaks for Monohydrate (S)-CSA salt of S-Ketamine

| position [°2θ] | d-spacing [Å] | relative intensity [%] |
|---|---|---|
| 7.76 | 11.38 | 58.03 |
| 8.11 | 10.89 | 21.58 |
| 12.75 | 6.94 | 24.89 |
| 13.13 | 6.74 | 55.99 |
| 13.31 | 6.65 | 23.96 |
| 13.64 | 6.49 | 31.52 |
| 14.92 | 5.93 | 100.00 |
| 15.51 | 5.71 | 32.12 |
| 15.71 | 5.64 | 28.46 |
| 18.45 | 4.80 | 43.84 |
| 24.22 | 3.67 | 25.66 |
| 25.26 | 3.52 | 28.46 |
| 27.33 | 3.26 | 51.32 |

% Water content was measured under adequate exclusion of atmospheric moisture using a modified volumetric Karl-Fischer titration for ketones, as follows. About 500 mg of the sample was weighed accurately and was dissolved in 40 mL of the Hydranal®-KetoSolver from Fluka (pre-titrated with the Karl-Fischer reagent Hydranal®-Composite 5K, from Fluka). Afterwards, the solution was titrated with the Karl-Fischer reagent. The endpoint was detected voltammetrically and the water content in percent was calculated according to the following formula:

Water content[%]=V*F*0.1/S where S represents Sample weight [g], F represents Factor of Karl-Fischer reagent [mg/mL], and V represents Consumption of Karl-Fischer reagent [mL].

The % water content was determined for multiple samples of crystalline monohydrate form of (S)-CSA salt of S-ketamine (prepared as described herein) with measured values ranging between 3.76% and 3.79% (average water content was 3.8%). The calculated theoretical value for a monohydrate of (S)-CSA salt of S-ketamine is 3.7%.

TG-FTIR measurement of a representative sample of the monohydrate crystalline form of (S)-CSA salt of S-ketamine exhibited a weight loss of 3.7 wt % in one step between 110° C. and 190° C. due to evaporation of water (corresponding to the theoretical 3.69 wt % stoichiometric water content of a monohydrate) and a chemical decomposition above 230° C.

The absolute optical rotation of multiple samples of monohydrate form of (S)-CSA salt of S-ketamine (prepared as described herein) was determined to range between 66.8° and 67.4°. Average absolute optical rotation was $[\alpha]^{20}_D=+67.8°$ (c=1.0, methanol).

Optical microscopy on the crystalline form of the monohydrate (S)-CSA salt of S-ketamine showed 1000-50 μM large equant crystals, appearing as fractured blocks. $^1$H NMR of a representative sample of the monohydrate (S)-CSA salt of S-ketamine confirmed the 1:1 salt stoichiometry.

DSC measured for a representative sample of the monohydrate (S)-CSA salt of S-ketamine exhibited a melting point of about 144° C., and a melting enthalpy of 121 J/g. DVS measurement of a representative sample of the monohydrate (S)-CSA salt of S-ketamine exhibited no hygroscopicity, and physical stability at elevated relative humidity.

The approximate solubility of the monohydrate crystalline form of the (S)-CSA salt of S-ketamine was measured by stepwise dilution of a suspension of about 10 mg of the sample in 0.05 mL solvent. Table 4 below lists the approximate solubility, denoted "S". If a sample was not dissolved by addition of a total of 10-12 mL of solvent, the solubility is indicated as <1 mg/mL in the Table 4, below.

TABLE 4

Approximate Solubility of Crystalline, Monohydrate Form of (S)-CSA salt of S-Ketamine

| Solvent or Mixture | Solubility (mg/mL) |
|---|---|
| acetone | 5 < S < 6 |
| anisole | S < 1 |
| DCM | 67 < S < 101 |
| 1,4-dioxane | 5 < S < 6 |
| DMF | 91 < S < 185 |
| DMSO | 106 < S < 212 |
| ethyl acetate | S < 1 |
| ethanol | 67 < S < 100 |
| heptane | S < 1 |
| acetonitrile | 22 < S < 24 |

TABLE 4-continued

Approximate Solubility of Crystalline, Monohydrate Form of (S)-CSA salt of S-Ketamine

| Solvent or Mixture | Solubility (mg/mL) |
|---|---|
| methanol | 226 < S |
| 2-methyl-THF | 5 < S < 7 |
| 2-propanol | 22 < S < 25 |
| isopropyl acetate | S < 1 |
| TBME | S < 1 |
| THF | 5 < S < 7 |
| toluene | S < 1 |
| water | 20 < S < 24 |
| 1:1 acetone:water | 58 < S < 77 |
| 10:1 aectobne:water | 20 < S < 24 |
| 2-methyl THF saturated with water | 6 < S < 8 |
| 1:1 2-propanol:water | 93 < S < 189 |
| 10:1 2-propanol:water | 24 < S < 28 |
| 1:1 2-propanol:isopropyl acetate | 10 < S < 11 |

Additionally, the solubility of the monohydrate crystalline form of the (S)-CSA salt of S-ketamine in select solvents was determined as follows: 21 g of (S)-CSA salt of S-ketamine was dissolved in 100 mL of solvent (as listed in Table 5 below). After 24 hours, the solutions were analyzed visually. If the compound was completely dissolved, solubility was above 20 g/100 mL. If the compound was not completely dissolved, any remaining precipitate was filtered off, the filtrate was diluted 400-fold with HPLC dilution solvent (or acetonitrile/HPLC dilution solvent) and analyzed by HPLC, with results as listed in Table 5, below.

TABLE 5

Solubility Measurements (S)-Ketamine-(+)-10-camphorsulfonate-monohydrate

| Solvent | Solubility [g/100 mL] at 23.6° C. |
|---|---|
| demineralized water | 5.344 |
| methanol | 18.457 |
| ethanol | 18.297 |
| 2-propanol | 7.275 |
| acetone (2-propanone) | 0.578 |
| N,N-dimethylacetamide | 18.200 |
| N,N-dimethylformamide | 18.267 |
| acetic acid | 18.209 |
| dichloromethane/methanol (50/50 v/v) | 18.589 |

The present invention is further directed to an amorphous form of the (S)-CSA salt of S-ketamine. In an embodiment of the present invention, the amorphous form of the (S)-CSA salt of S-ketamine is anhydrous.

The amorphous, anhydrous form of the (S)-CSA salt of S-ketamine may be prepared by dehydrating the monohydrate form at an elevated temperature, for example at a temperature greater than about 120° C. In an example, a sample of the monohydrate crystalline form of (S)-CSA salt of S-ketamine was maintained at 160° C. under dry nitrogen flow for 30 min. pXRD analysis carried out several hours later showed a mixture of the crystalline monohydrate and amorphous anhydrous forms of (S)-CSA salt of S-ketamine. The amorphous anhydrous form of (S)-CSA salt of S-ketamine was also obtained (in a mixture with the monohdrate form) by slurrying the crystalline monohydrate form of (S)-CSA salt of S-ketamine in 2-methyl THF or isopropyl acetate at about 80° C. for about 4 days. The amorphous, anhydrous form of (S)-CSA salt of S-ketamine is hygroscopic and rapidly converts to the monohydrate form of (S)-CSA salt of S-ketamine on storage at ambient conditions.

The present invention further comprises pharmaceutical compositions containing a product prepared according to any of the process(es) described herein with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above.

The pharmaceutical compositions herein will contain, per unit dosage unit, e.g., tablet, capsule, powder, injection, suppository, teaspoonful, and the like, of from about 0.01 mg to about 1000 mg or any amount or range therein, and may be given at a dosage of from about 0.01 mg/kg to about 1.5 mg/kg, or any amount or range therein, preferably from about 0.01 mg/kg/day to about 0.75 mg/kg, or any amount or range therein, preferably from about 0.05 mg/kg to about 0.5 mg/kg, or any amount or range therein, preferably from about 0.1 mg/kg to about 0.5 mg/kg, or any amount or range therein, of each active ingredient. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 mg to about 1,000 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating treatment resistant depression described in the present invention may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein; preferably from about 0.05 mg to about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a product prepared according to any of the process(es) as described herein as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

Preparation of (S)-Ketamine (+)-CSA Monohydrate Salt

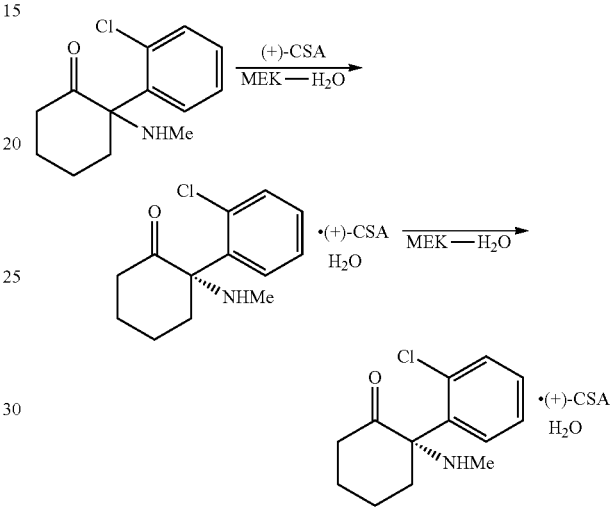

rac-Ketamine free base (10 g, 42 mmol) and (+)-CSA (10 g, 42 mmol, 98 mass %, 1 eq.) in methyl ethyl ketone (33.3 g) and water (1.85 g) were stirred at room temperature. The reaction mixture was then heated 50° C. and stirred for 1 h at this temperature. The resulting slurry was cooled to room temperature over 1 h. The resulting suspension stirred overnight and filtered. The wet cake was washed twice with methyl ethyl ketone (5 g) to yield the title compound as a white solid (10.15 g of wet product). The material was dried for 6 h at 50° C., 10 mbar to yield (S)-Ketamine CSA salt as a white solid.

Yield: 10.04 g

Purity: HPLC: 100%,

Enantiomeric purity: 96.4%

Assay corrected yield: 49%

Example 2

Recrystallization of (S)-Ketamine (+)-CSA Monohydrate Salt

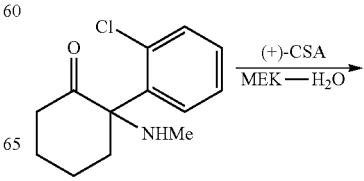

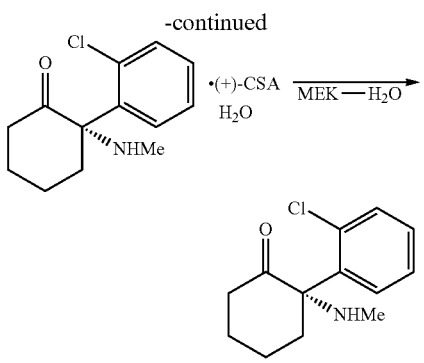

To (S)-ketamine-(+)-CSA monohydrate salt (10.1 g, 41.3 mmol) were added methyl ethyl ketone (33.3 g) and water (1.85 g). The reaction mixture was then warmed to 80° C. A clear solution was observed to form. The reaction mixture was then cooled to 50° C. (a slurry was observed to form). At this temperature, additional methyl ethyl ketone (33.3 g) was added. The resulting suspension was cooled to 20° C. over 1 h. The resulting suspension was stirred overnight and filtered. The wet cake was washed twice with methyl ethyl ketone (5 g) to yield the title compound as a white solid (8.84 g of wet product). The material was dried for 1 h at 50° C., 10 mbar to yield (S)-Ketamine CSA salt as a white solid.

Yield: 8.81 g
Purity: HPLC: 100%
Enantiomeric purity: 100%
Assay corrected yield: 86%

Example 3

Preparation of (S)-Ketamine (+)-CSA Monohydrate Salt

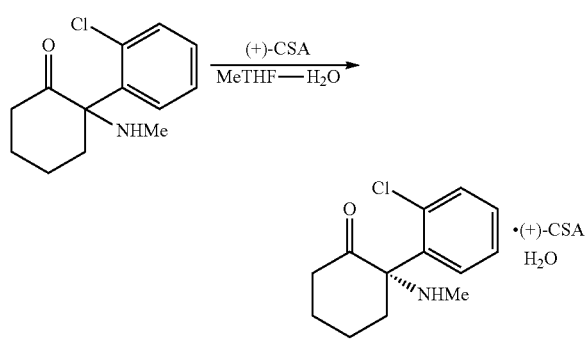

rac-Ketamine free base (10 g, 42 mmol) and (+)-CSA (9.8 g, 42 mmol, 1 eq.) in 2-methyl-THF (70 g) were stirred at room temperature. Water (6.3 g) was added to yield a slurry. The slurry was heated to reflux (T=73° C.), resulting in the formation of a clear solution. The solution was stirred at reflux temperature for 1 h, then cooled to 63° C. and seeded with small amounts (one spatula tip) of (S)-Ketamine-CSA salt. Crystallization was observed to start. The suspension was maintained at this temperature for 1 h, cooled in 1 h to 50° C. and then to 20° C., over an additional one hour. The resulting suspension was stirred overnight and filtered. The wet cake was washed twice with 2-methyl-THF (10 g) to yield the title compound as a white solid (9.1 g of wet product). The material is dried overnight at 50° C., 20 mbar to yield (S)-Ketamine CSA salt as a white solid.

Yield: 9.06 g
Purity: HPLC: 100%,
Enantiomeric purity: 99.3%
Assay corrected yield: 45%

Example 4

Preparation of (S)-Ketamine (+)-CSA Monohydrate Salt

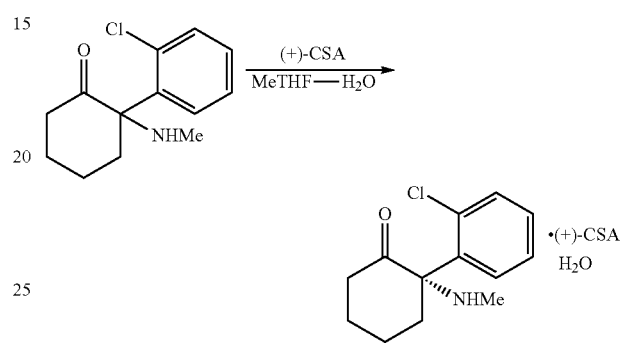

rac-Ketamine free base (600 g, 2.524 mol) (+)-CSA (588 g, 2.531 mol, 1 eq) in 2-Me-THF (4200 g) were stirred at room temperature. Then water (378 g) was added (formation of a slurry was observed). The slurry was heated to reflux (T=72-73° C.). A clear solution was observed to form. The solution was stirred at this temperature for about 10 minutes. The mixture was cooled to 63° C. within 20 min and seeded with (S)-Ketamine-(+)-CSA monohydrate salt (2 g). Crystallization was observed to start. The resulting suspension was maintained at this temperature for 1 h. Then the following cooling profile was applied: cooling to 59° C. in 1 h, cooling to 52° C. in 1 h, cooling to 38° C. in 1 h, cooling to 20° C. in 40 min, cooling to 0° C. in 20 min. The suspension was stirred for 6 h-16 h and filtered. The wet cake was washed with 2-Me-THF (a total of 2150 g) containing 2% of water (2107 g 2-Me-THF, 43 g water) in 3 portions and wet product were obtained as white solid (654 g). The material was dried overnight at 50° C. at 20 mbar and (S)-Ketamine CSA salt monohydrate (573 g) was obtained as white solid.

Enantiomeric purity: 99.21
Assay corrected yield: 47%
Water content: 3.84%

Example 6

Recrystallization of (S)-Ketamine (+)-CSA Monohydrate Salt

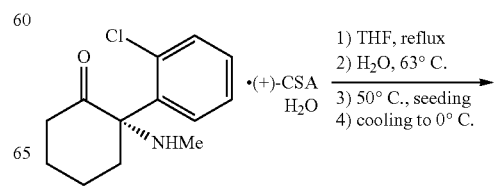

27

-continued

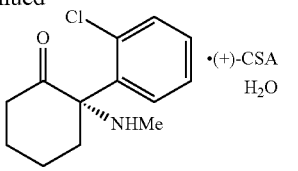

(S)-Ketamine-(+)-CSA monohydrate (50.0 g, 102.46 mmol) was suspended in THF (375 g) and water (25 g). The resulting mixture was heated to reflux (clear solution, T=64° C.). The clear solution was cooled to 50° C. and seeded with crystals of (S)-Ketamine-(+)-CSA monohydrate (0.25 g). Crystallization was observed to start and a suspension was formed, which was stirred for 1 h at this temperature. The suspension was cooled to 0° C. within 8 h and stirred for overnight at this temperature. The product was filtered off and washed with THF (3×25 g). The wet product (45.8 g) was dried overnight at 50° C. at 20 mbar to yield (S)-Ketamine-(+)-CSA monohydrate are isolated as white solid (45.4 g).
Enantiomeric Purity: 100.00
Assay Corrected Yield: 91%
Water Content: 3.84%

Example 7

Preparation of (R)-Ketamine (−)-CSA Monohydrate Salt

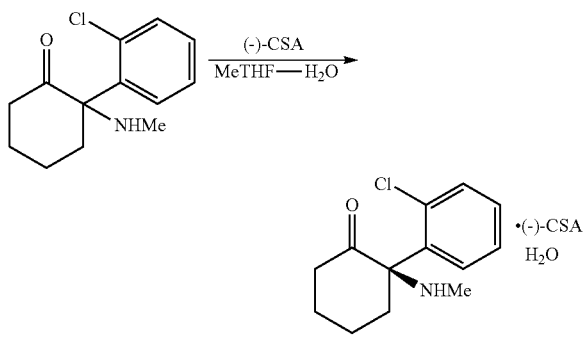

rac-Ketamine free base (10 g, 42 mmol) and (−)-CSA (9.8 g, 42 mmol, 1 eq.) in 2-methyl-THF (70 g) were stirred at room temperature. Water (6.3 g) was added to yield a slurry. The slurry was heated to reflux (T=72° C.), resulting in the formation of a clear solution. The solution was stirred at reflux temperature for 1 h, then cooled to 63° C. 0.5 ml of a suspension prepared from 100 mg (R)-ketamine, and 98 mg (−)-camphor-10-sulfonic acid dissolved in 1.5 g of THF and 8 μg of water (spontaneous crystallization) was added. The reaction mixture became turbid. The formed suspension was cooled to 59° C. within 1 h, then further cooled in 1 h to 52° C., in 1 h to 38° C., in 2 h to 20° C., and in 2 h to 0° C. The formed suspension was further stirred at 0° C. overnight. The resulting suspension was filtered, and the wet cake was washed twice with a mixture of 2-methyl-THF (9.6 g) and water (0.4 g) to yield the title compound as a white solid (10.5 g of wet product). The material was dried overnight at 50° C., 20 mbar to yield (R)-Ketamine (−)-CSA salt as a white solid.
Yield: 9.3 g; Assay corrected yield: 43%
Purity: HPLC: 100%;
Enantiomeric purity: 99.38%, purity 100%, assay 95.23%

28

Example 8

Preparation of (S)-Ketamine Hydrochloride Salt from the Mother Liquor of Example 7

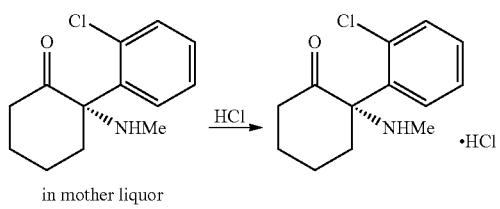 [SMILES: CN[C@]1(c2ccccc2Cl)CCCCC1=O ; Cl ; CN[C@]1(c2ccccc2Cl)CCCCC1=O ; Cl]

in mother liquor

To the mother liquor of Example 7 (which contains (S)-ketamine and (−)-camphor-10-sulfonic acid dissolved in a methyl-THF/water mixture (10.9:1)) was added HCl gas (0.9 g) at ambient temperatures over 2 min. Spontaneous crystallization of a solid was observed (pH of the solution 0-1). After stirring for 30 min the solids were filtered off, and the wet cake was rinsed twice with methyl-THF (5.0 g each time). The resulting solids (5.8 g wet) were dried in vacuum at 50° C.
The mother liquor (107.45 g) contains 82% (S)-ketamine and 18% (R)-ketamine.
Yield 3.91 g; Assay Corrected Yield (with respect to the used rac-ketamine in experiment 7: 34% (68% with respect to (S)-ketamine)
Enantiomeric Purity: 99.78%
Water Content: 0.23%, purity 99.98%, assay 97.56%

Example 9

Classical Resolution Screening Experiments

Unless otherwise noted, all resolution experiments were performed on a 1 mmol scale of (±)-ketamine free base and with addition of 0.5 mol-equivalent of the selected acidic resolving agent in 3.5 mL of solvent. The acidic resolving agents tested were as follows:

| ID No. | Structure/Name |
|---|---|
| 1 | ![structure] <br> (1S)-(+)-10-camphorsulphonic acid |
| 2 | ![structure] <br> (S)-(−)phencyphos (P1(+)) |

-continued
| ID No. | Structure/Name |
|---|---|
| 3 | 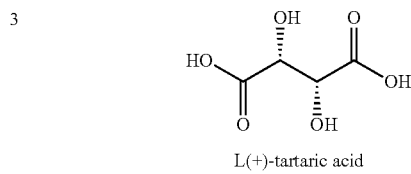<br>L(+)-tartaric acid |
| 4 | 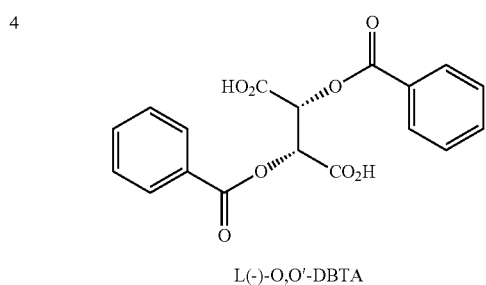<br>L(−)-O,O′-DBTA |
| 5 | 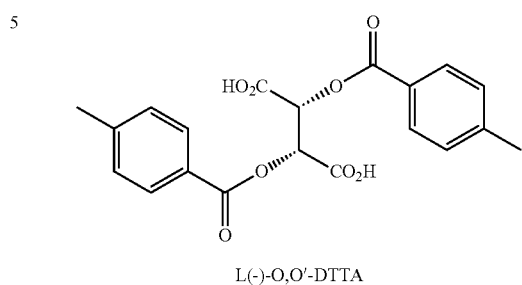<br>L(−)-O,O′-DTTA |
| 6 | 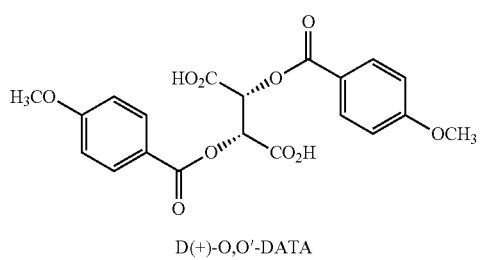 [SMILES: COc1ccc(C(=O)O[C@@H](C(=O)O)[C@@H](OC(=O)c2ccc(OC)cc2)C(=O)O)cc1]<br>D(+)-O,O′-DATA |
| 7 | 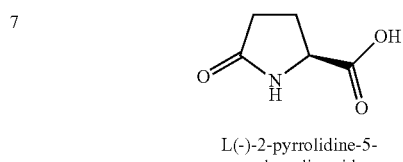<br>L(−)-2-pyrrolidine-5-carboxylic acid |
| 8 | 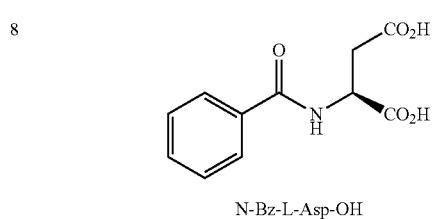<br>N-Bz-L-Asp-OH |
-continued
| ID No. | Structure/Name |
|---|---|
| 9 | 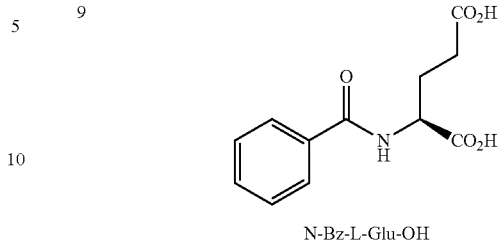<br>N-Bz-L-Glu-OH |
| 10 | 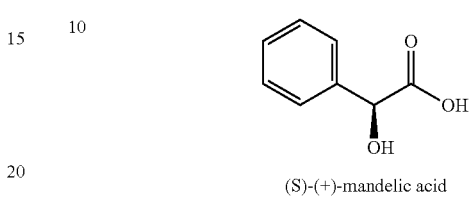<br>(S)-(+)-mandelic acid |
| 11 | 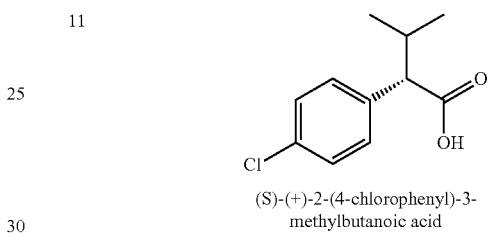<br>(S)-(+)-2-(4-chlorophenyl)-3-methylbutanoic acid |
| 12 | 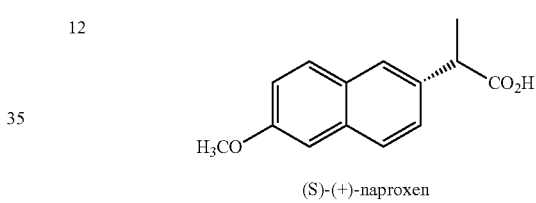<br>(S)-(+)-naproxen |
| 13 | 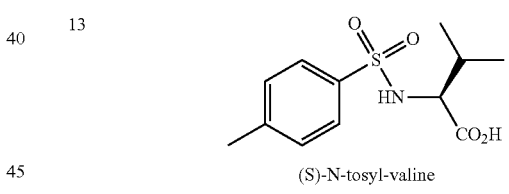<br>(S)-N-tosyl-valine |
| 14 | 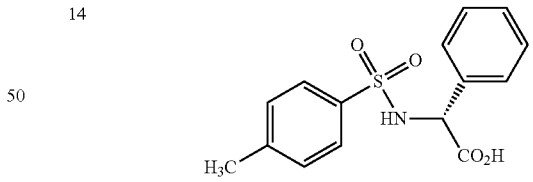<br>(R)-N-Tosyl-phenylglycine |
| 15 | 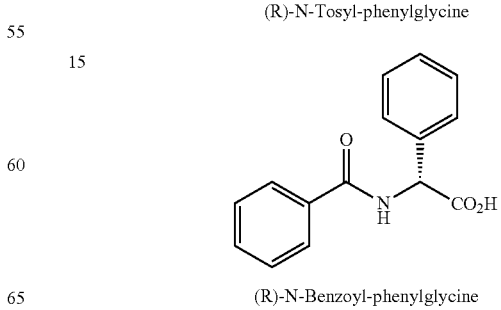<br>(R)-N-Benzoyl-phenylglycine |

| ID No. | Structure/Name |
|---|---|
| 16 | (R)-(-)-1,1'-bisnaphthyl-2,2'-diyl-hydrogenphosphate |

Preparation of (±)-ketamine Free Base

Racemic ketamine.HCI (15.0 g, 54.7 mmol) was dissolved in 100 mL of water under stirring. To the solution was added 100 mL CHCl$_3$ and under vigorous stirring basified by drop-wise addition of a solution of 2.40 g NaOH (60 mmol) in 30 mL of water. The white precipitate that was formed was directly extracted into the CHCl$_3$ layer (clear solution). The mixture was transferred into a separation funnel and separated. The aqueous phase was extracted again with 100 mL chloroform and then with 50 mL of chloroform. The combined chloroform layers were washed with 50 mL of water, dried over Na$_2$SO$_4$ and concentrated on a Rotavap to yield a white crystalline solid (solidified oil). Yield: 12.88 g of white solid (54.2 mmol, 99%); NMR confirmed ketamine free base.

The procedure was repeated with 10.15 g (36.9 mmol) of racemic ketamine and yielded 8.73 g (36.7 mmol, 99.5%) of free ketamine as a white solid.

RS1: Resolution Screening Experiments in Methanol:

Ketamine free base (3.93 g, 16.5 mmol) was dissolved in 15 mL methanol (slightly warmed for dissolution), transferred to a 25 mL volumetric flask and the flask filled to 25 mL with methanol (1 mmol=1.52 mL). The weight of this solution was 21.0 g (1 mmol=1.27 g). The resolving agent was dissolved/suspended in 1.60 g (2.0 mL) of methanol.

At room temperature 1.27 g (1.0 mmol) of the prepared ketamine free base solution in methanol was added to the prepared resolving agent in methanol mixture. All resulting solutions were observed to become clear, except Exp. #1.2 and #1.9, which were heated to effect dissolution. After standing for 22 h at room temperature, all solutions were still clear. The screw caps were removed after 2 days, to allow slow evaporation. After 5 days, most of the solvent was evaporated and in most vials a thick oil remained, as indicated in Table RS1, below. To the vials with a solid layer was added 1 mL of MeOH to re-dissolve any solids. Addition of the methanol resulting in most of the solid re-dissolving, and then 3 mL of cyclo-pentyl methyl ether (CPME) as anti-solvent was added. After 4 hours standing, all vials were again opened again for slow evaporation. After 2 days slow evaporation of the CPME to ~2 mL, a thick turbid oil was observed to form in some of the vials (see Table RS1). These vials were closed and heated to reflux for dissolution (if necessary a few drops of MeOH were added for dissolution). In vials of Exp. #1.4, #1.5 and #1.9 oils were formed again. In vial of Exp. #1.16 a solid was formed and the mother liquid (and 0.5 mL CPME washing) was removed with a pipette, although the solid exhibited an e.e. <5%. Vials/experiments which did not yield a solid after 7 days (with addition of CPME as anti-solvent) were held at room temperature for up to an additional 7 days (total of 14 days) in an effort to effect crystallization.

Table 6 below summarized the conditions and results of screening experiments with the 16 resolving agents identified above, using methanol as the solvent. Note: in experiments where no observation is noted in the columns "5-day evaporation" and/or "7 days+CPME, up to 14 days", no solid or oil was obtained.

TABLE 6

Resolution Screening Results, MeOH solvent

| Exp # | Resolving Agent | mg* (0.5 mmol) | 5 day evaporation | 7 days + CPME, up to 14 days |
|---|---|---|---|---|
| 1.1 | (1S)-(+)-10-camphorsulfonic acid | 116 | | |
| 1.2 | (S)-(+)-phencyphos (P1(+)) | 121 | solid | |
| 1.3 | L(+)-tartaric acid | 75 | | 8 days: turbid (oil layer) 14 d: solidified |
| 1.4 | L(-)-O,O'-DBTA | 188 | | 9 days: turbid oil |
| 1.5 | L(-)-O,O'-DTTA | 193 9 | | 9 days: turbid oil |
| 1.6 | D(+)-O,O'-DATA | 209 | | 9 days: turbid oil(clear after heating + MeOH) |
| 1.7 | L(-)-2-pyrrolidone-5-carboxylic acid | 65 | 5 d: solid (needles) + MeOH: re-dissolved | 8 days: turbid oil (clear after heating + MeOH) |
| 1.8 | N-Bz-L-Asp-OH | 119 | | 9 days: turbid oil |
| 1.9 | N-Bz-L-Glu-OH | 126 | solid | turbid oil after addition CPME |
| 1.10 | (S)-(+)-mandelic acid | 76 | | |
| 1.11 | (S)-(+)-2-(4-chlorophenyl)-3-methylbutanoic acid | 106 | solid | 14 days: solid in oil after evaporation |
| 1.12 | (S)-(+)-Naproxen | 115 | solid + MeOH: re-dissolved | |
| 1.13 | (S)-N-Tosyl-valine | 136 | solid | |
| 1.14 | (R)-N-Tosyl-phenylglycine | 153 | solid | |

TABLE 6-continued

Resolution Screening Results, MeOH solvent

| Exp # | Resolving Agent | mg* (0.5 mmol) | 5 day evaporation | 7 days + CPME, up to 14 days |
|---|---|---|---|---|
| 1.15 | (R)-N-Benzoylphenylglycine | 128 | solid | |
| 1.16 | (R)-(−)-1,1'-bisnaphthyl-2,2'-diyl hydrogenphosphate | 87** | | 9 days: turbid oil, crystallized after heating Solid: 78 mg e.e. <5% ML: e.e. <5% |

*+/−1 mg;
**0.25 mmol resolving agent in 1 mL methanol, added 0.64 g (0.50 mmol) ketamine MeOH solution In summary: no crystals were obtained when methanol was used as the solvent. After evaporation of methanol, the obtained oils were re-dissolved in a small amount of methanol and CPME (as anti-solvent). In three experiments, #1.3, #1.11 and #1.16 some solids were obtained. For Exp. #1.1, the % ee of the mother liquor and solid were determined to be very low (<5%).

RS2: Resolution Screening Experiments in 2-butanone (MEK)

Ketamine free base (3.93 g, 16.5 mmol) was dissolved in 15 mL 2-butanone (slightly warmed for dissolution), transferred to a 25 mL volumetric flask and the flask filled to 25 mL with 2-butanone (1 mmol=1.52 mL). The weight of this solution was 21.29 g (1 mmol=1.29 g). The resolving agent was dissolved/suspended in 1.60 g (2.0 mL) of 2-butanone.

At room temperature 1.29-1.32 g (1.0 mmol) of the prepared ketamine solution in 2-butanone was added to the prepared resolving agent solution. All solution became clear, except vials in Exp. #2.3, #2.6, #2.7, #2.8, #2.9, #2.14 and #2.15. These vial were heated for dissolution. In vials of Exp. #2.3 and #2.9 some solid remained, whereas vials for Exp. #2.14 and #2.15 became opaque. After 20 h at room temperature, the vials of Exp. #2.3 (tartaric acid), #2.7 (pyroGlu) and #2.9 (N-BzGlu) contained some crystals. The solution in vials of Exp. #2.14 and #2.15 became slightly turbid. In all other vials the solution remained clear, therefore after 2 days, the screw caps of these vials were removed for slow evaporation. After 5 days slow evaporation to half volume no additional crystallization was observed to occur. After 7 days the clear solutions in vials of Exp #2.4 and #2.5 were seeded with the L-(−)-DATA salt of S-ketamine (prepared as described in RS5: #4.2 which follows), however, no crystallization occurred and the seed crystals dissolved. Vials/experiments which did not yield a solid after 7 days were held at room temperature for up to an additional 7 days (total of 14 days) in an effort to effect crystallization.

Table 7 below summarized the results of screening experiments with 16 resolving agents and 2-butanone as the solvent. NOTE: Where no observation is noted in the columns "20 h room temperature", "5-day slow evapor." and/or "7-14 days", no solid or oil was obtained.

TABLE 7

Resolution Screening Results, 2-Butanone (MEK)

| Exp # | Resolving agent | mg (0.5 eq.) | 20 h RT | 5 day, slow evapor. | 7-14 days |
|---|---|---|---|---|---|
| 2.1 | (1S)-(+)-10-camphorsulfonic acid | 116 | | | |
| 2.2 | (S)-(+)-phencyphos (P1(+)) | 121 | | | |
| 2.3 | L(+)-tartaric acid | 75 | crystals | | 8 days: Solid: 183 mg e.e. 58% (S) ML: e.e. 31% (R) |
| 2.4 | L(−)-O,O'-DBTA | 188 | | | |
| 2.5 | L(−)-O,O'-DTTA | 193 | | | |
| 2.6 | D(+)-O,O'-DATA | 209 | crystals @ 24 h | | 8 days: Solid: 245 mg e.e. 61% (S) ML: e.e. 32% (R) |
| 2.7 | L(−)-2-pyrrolidone-5-carboxylic acid | 65 | few crystals | thick oil | |
| 2.8 | N-Bz-L-Asp-OH | 119 | | 8 d: few crystals | |
| 2.9 | N-Bz-L-Glu-OH | 126 | crystals | | 8 days: Solid: 149 mg e.e. <5% ML: e.e. <5% |
| 2.10 | (S)-(+)-mandelic acid | 76 | | | |
| 2.11 | (S)-(+)-2-(4-chlorophenyl)-3-methylbutanoic acid | 106 | | 8 d: few crystals | |
| 2.12 | (S)-(+)-Naproxen | 115 | | | |
| 2.13 | (S)-N-Tosyl-valine | 136 | | | |
| 2.14 | (R)-N-Tosyl-phenylglycine | 153 | turbid | | 8 days: turbid |
| 2.15 | (R)-N-Benzoylphenyl-glycine | 128 | turbid | pink solution | |
| 2.16 | (R)-(−)-1,1'-bisnaphthyl-2,2'-diyl hydrogen phosphate | 87** | | | |

*+/−1 mg;
**0.25 mmol resolving agent in 1 mL 2-butanone, added 0.66 g (0.50 mmol) ketamine solution As shown in Table 7 above, when 2-butanone was used as the solvent, L-(+)-tartaric acid and D-(+)—O, O'-DATA yielded a solid, with some resolution of the (S)- and (R)-ketamine stereoisomers. Although D-(+)—O, O'-DATA yielded a solid, the solid was determined (by $^1$H NMR) to be a 1:1 salt of the undesired enantiomer, containing 1 mol of 2-butanone as a solvate molecule. Additionally, N-Bz-L-

Glu-OH yielded a solid, although analysis of this solid indicated that no significant amount of resolution was achieved.

RS3: Resolution Screening Experiments in 10:1 v:v IPA/H$_2$O

Ketamine free base (3.93 g, 16.5 mmol) was dissolved in a 10:1 v:v mixture of 2-propanol/water to a total volume of 25 mL (warmed for dissolution and kept hand warm to prevent crystallization). The weight of this solution was 21.1 g (1 mmol=1.27 g=1.52 mL). The resolving agent was dissolved/suspended in 1.60 g (2.0 mL) of a 10:1 v:v mixture of 2-propanol/water.

At room temperature 1.27-1.30 g (1.0 mmol) of the prepared ketamine solution was added to the prepared resolving agent solution, except Exp #3.12 where 1.43 g (1.12 mmol) of the prepared ketamine solution was added to the corresponding prepared resolving agent solution. The resulting solutions became clear, except Exp #3.2, #3.3, #3.5, #3.6, #3.9, #3.14 and #3.15 which were heated for dissolution. In the vial of Exp. #3.9 some solid remained even after heating. After 18 h at room temperature only the vial of Exp. #3.9 contained some crystals (possibly the resolving agent) and the vial of Exp. #3.15 became slightly turbid. In all other vials the solution remained clear, therefore the screw caps were removed for slow evaporation to half volume over 5 days. In 4 vials a crystal ring was formed on the glass wall above the surface (possible Marangoni-like effect) that was scratched back into the mother liquid. For Exp #3.8 these crystals were observed to re-dissolve. Vials/experiments which did not yield a solid were held at room temeprature for up to a total of 14 days, in an effort to effect crystallization. Table 8 below summarized the results of screening experiments with 16 resolving agents and the 10:1 v:v mixture of IPA:water as the solvent. Note: Where no observation is noted in the columns "18 h RT", "5 day, slow evap." and/or "6-14 day", no solid or oil was obtained.

TABLE 8

Resolution Screening Results, 10:1 v:v IPA/H$_2$O

| Exp # | Resolving agent | mg (0.5 eq) | 18 h RT | 5 day slow evap. | 6-14 days |
|---|---|---|---|---|---|
| 3.1 | (1S)-(+)-10-camphorsulfonic acid | 116 | | | |
| 3.2 | (S)-(+)-phencyphos (P1(+)) | 121 | | | |
| 3.3 | L(+)-tartaric acid | 75 | | | |
| 3.4 | L(−)-O,O'-DBTA | 188 | | | |
| 3.5 | L(−)-O,O'-DTTA | 193 | | | |
| 3.6 | D(+)-O,O'-DATA | 209 | | | |
| 3.7 | L(−)-2-pyrrolidone-5-carboxylic acid | 65 | | crystal ring | 8 days: Solid: 71 mg e.e. <5% ML: e.e. <5% |
| 3.8 | N-Bz-L-Asp-OH | 119 | | crystal ring, re-dissolved in ML | |
| 3.9 | N-Bz-L-Glu-OH | 126 | few crystals | crystal ring | 8 days: Solid: 92 mg e.e. <5% ML: e.e. <5% |
| 3.10 | (S)-(+)-mandelic acid | 76 | | | |
| 3.11 | (S)-(+)-2-(4-chlorophenyl)-3-methylbutanoic acid | 106 | | 6 d: slow crystallization (needles) | 8 days: Solid: 83 mg e.e. <5% ML: e.e. <5% |
| 3.12 | (S)-(+)-Naproxen | 115 | | 6 d: slow crystallization (needles) | 8 days: Solid: 103 mg e.e. <5% ML: e.e. <5% |
| 3.13 | (S)-N-Tosyl-valine | 136 | | | |
| 3.14 | (R)-N-Tosyl-phenylglycine | 153 | | | Turbid |
| 3.15 | (R)-N-Benzoyl-phenylglycine | 128 | turbid | crystal ring | 8 days: Solid: 39 mg e.e. <5% ML: e.e. <5% |
| 3.16 | (R)-(−)-1,1'-bisnaphthyl-2,2'-diyl hydrogen phosphate | 87** | | | |

*+/−1 mg;
**0.25 mmol resolving agent in 1 mL 2-PrOH/H2O 10:1, added 0.65 g (0.50 mmol) ketamine solution As shown in Table 8 above, when a 10:1 v:v IPA/water mixture was used as the solvent, L(−)-2-pyrrolidone-5-carboxylic acid, N-Bz-L-Glu-OH, (S)-(+)-2-(4-chlorophenyl)-3-methylbutanoic acid, (S)-(+)-Naproxen and (R)-N-Benzoyl-phenylglycine yielded a solid, although analysis of said solids indicated that no significant amount of resolution was achieved for any of these resolving agents.

RS4: Preparation of L-(−)-DATA salt of S-Ketamine

Ketamine (racemic, 238 g, 1 mmol) was dissolved in MEK (3,5 mL) and the resulting solution was added to dry L-(−)-DATA (0.5 mmol). The mixture (in a vial) was warmed to reflux to complete dissolution and then cooled.

Slow crystallization started after 24 hours (scratching with spatula), to yield a solid (167 mg, 23%) which exhibited 54% e.e.

The resolution screening experiments described above confirmed that L-tartaric acid is useful as a resolving agent for ketamine, and suggested that D-(+)-DATA, and L-(−)-DATA (derivatives of tartaric acid), may also be effective.

Although additional optimization experiments with D-(+)-DATA and L-(−)-DATA were completed, for large scale manufacturing, material costs for these resolving agents are not cost-effective and/or prohibitive.

Example 10

Resolution Experiments (+)-CSA in Organic Solvent/Water Mixture

Although contrary to the results of the screening experiments described above and contrary to the teachings in HUDYMA, T. W., et al. (DE 2062620 A), which disclosed that attempts at resolution of ketamine with cam phorsulfonic acid (CSA) were unsuccessful, additional experiments were nonetheless undertaken in an effort to develop a method for the resolution of ketamine using cam phorsulfonic acid in aqueous solvent mixture.

Table 9 below details three representative experiments reacting racemic ketamine with (+)-CSA in (a) a mixture of THF and water, (b) a mixture of acetone and water, and (c) a mixture of 2-methyl-THF and water. Each experiment resulted in formation of (S)-ketamine•(+)-CSA salt in high enantiomeric excess, as noted in the Table below. All reaction mixtures were heated, with stirring as noted. The resulting precipitate was then isolated by filtration, washed with the corresponding organic solvent (no water) and dried at under vacuum 50° C.

TABLE 9

Preparation of (+)-CSA salt of S-Ketamine

|  | E-1 | E-2 | E-3 |
|---|---|---|---|
| (Rac)-Ketamine | 10 g | 5 g | 10 g |
| (+)-CSA | 5.3 g | 2.65 g | 9.8 g |
| Solvent | 60 g THF + 1.2 g H$_2$O | 40 g Acetone + 2.5 g H$_2$O | 60 g 2-Me—THF + 3.8 g H$_2$O |
| Rxn Conditions | 63° C. for 30 min; 50° C., 1 hr; 20° C., 2 hr; stirred overnight; | 55° C.; 10° C., 2 hr cooling; 10° C., 30 min, stirring; continued stirring overnight; | 73° C.; mixture not dissolved; add 10 g 2-Me—THF + 1.9 g H$_2$O; 63° C., seeded & stirred for 1 hr; 50° C. 1 hr, 20° C. 1 hr, 2 hr stirring |
| Notes: | first crystallization observed during heating to 63° C. | crystallization observed at 42° C. | Seeded at 63° C. |
| Yield[a] | 8.12 g (39.4%) | 3.53 g (34.3%) | 9.24 g (44.6%) |
| % ee | 97.3% ee | 98.0% ee | 98.4% ee |

[a]Maximum yield of desired product (S-enantiomer) from racemate is 50%.

Formulation Example 1

Solid, Oral Dosage Form—Prophetic Example

As a specific embodiment of an oral composition, 100 mg of a product prepared as in Example 1, 2 or 3 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed:

1. A process for the preparation of a monohydrate form of (S)-camphorsulfonic acid salt of S-ketamine comprising

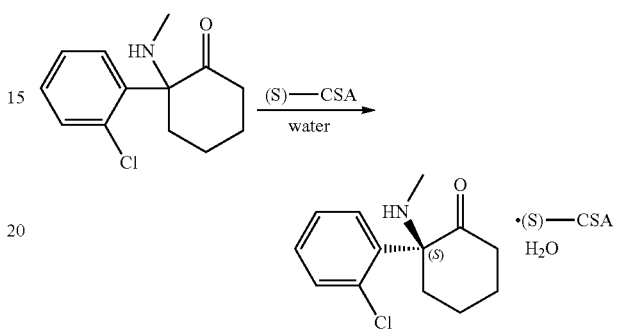

reacting ketamine with (S)-camphorsulfonic acid, wherein the (S)-camphorsulfonic acid is present in an amount in the range of from about 0.5 to about 2.0 molar equivalents (relative to the molar amount of ketamine);
　in the presence of water, wherein the water is present in an amount in the range of from about 3.5% to about 15%;
　in an organic solvent selected from the group consisting of an ether, a ketone, and mixtures thereof; at a temperature in the range of from about 20° C. to about solvent reflux temperature;
　to yield the corresponding monohydrate form of (S)-camphorsulfonic acid salt of S-ketamine;
　wherein the monohydrate form of (S)-camphorsulfonic acid salt of S-ketamine is present in an enantiomeric excess in the range of from about 50% to about 100%.

2. The process of claim 1, wherein the (S)-camphorsulfonic acid is present in an amount in the range of from about 0.75 to about 1.2 molar equivalents.

3. The process of claim 1, wherein the (S)-camphorsulfonic acid is present in an amount in the range of from about 0.9 to about 1.1 molar equivalents.

4. The process of claim 1, wherein the water is present in an amount in the range of from about 5% to about 10%.

5. The process of claim 1, wherein the water is present in an amount in the range of from about 6% to about 8%.

6. The process of claim 1, wherein the organic solvent is selected from the group consisting of methyl ethyl ketone and 2-methyl-THF.

7. The process of claim 1, wherein the organic solvent is 2-methyl-THF.

8. The process of claim 1, wherein the ketamine is reacted with (S)-camphorsulfonic acid at a temperature in the range of from about 30° C. to about 100° C.

9. The process of claim 1, wherein the ketamine is reacted with (S)-camphorsulfonic acid at a temperature of about 50° C. to about 80° C.

10. The process of claim 1, wherein the monohydrate form of (S)-camphorsulfonic acid salt of S-ketamine is present in an enantiomeric excess in the range of from about 75% to about 100%.

11. The process of claim 1, wherein the monohydrate form of (S)-camphorsulfonic acid salt of S-ketamine is present in an enantiomeric excess in the range of from about 90% to about 100%.

12. The process of claim 1, wherein the monohydrate form of (S)-camphorsulfonic acid salt of S-ketamine is present in an enantiomeric excess of greater than or equal to about 96%.

13. A process for the preparation of a monohydrate form of (S)-camphorsulfonic acid salt of S-ketamine comprising

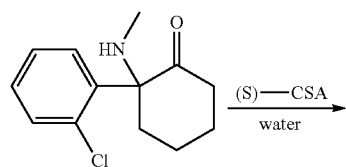

-continued

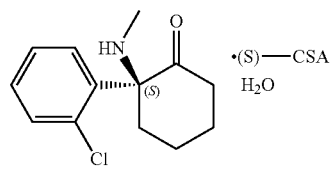

reacting racemic ketamine with (S)-camphorsulfonic acid, wherein the (S)-camphorsulfonic acid is present in an amount of about 1 molar equivalents (relative to the molar amount of ketamine);

in the presence of water, wherein the water is present in an amount in the range of from about 6% to about 8%;

in 2-methyl-THF; at a temperature of about 70° C.;

to yield the corresponding monohydrate form of (S)-camphorsulfonic acid salt of S-ketamine;

wherein the monohydrate form of (S)-camphorsulfonic acid salt of S-ketamine is present in an enantiomeric excess in the range of from about 80% to about 100%.

14. The process of claim 1, further comprising (a) reacting the monohydrate form of (S)-camphorsulfonic acid salt of S-ketamine with a base; in a solvent or mixture of solvents; to yield S-ketamine as a free base; and (b) reacting the S-ketamine free base with HCL; to yield the corresponding S-ketamine hydrochloride salt.

15. The process of claim 1, wherein the organic solvent is selected from the group consisting of THF, 2-methyl-THF, methyl ethyl ketone, acetone, methyl isobutyl ketone, and mixtures thereof.

* * * * *